(12) United States Patent
Sharifi et al.

(10) Patent No.: US 9,856,536 B2
(45) Date of Patent: Jan. 2, 2018

(54) METHOD FOR TREATING CASTRATION-RESISTANT PROSTATE CANCER

(71) Applicant: THE CLEVELAND CLINIC FOUNDATION, Cleveland, OH (US)

(72) Inventors: Nima Sharifi, Shaker Hts., OH (US); Kai-Hsiung Chang, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 227 days.

(21) Appl. No.: 14/330,177

(22) Filed: Jul. 14, 2014

(65) Prior Publication Data

US 2015/0018323 A1 Jan. 15, 2015

Related U.S. Application Data

(60) Provisional application No. 61/846,344, filed on Jul. 15, 2013.

(51) Int. Cl.
| | |
|---|---|
| *C12Q 1/68* | (2006.01) |
| *A61K 31/56* | (2006.01) |
| *G01N 33/574* | (2006.01) |
| *G01N 33/573* | (2006.01) |
| *G01N 33/53* | (2006.01) |
| *A61K 31/58* | (2006.01) |
| *A61K 31/4166* | (2006.01) |

(52) U.S. Cl.
CPC ........ *C12Q 1/6886* (2013.01); *A61K 31/4166* (2013.01); *A61K 31/58* (2013.01); *G01N 33/57434* (2013.01); *C12Q 2600/106* (2013.01); *C12Q 2600/156* (2013.01); *C12Q 2600/158* (2013.01); *G01N 2333/904* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 7,858,306 B2 * | 12/2010 | Weinshilboum | ..... C12N 9/0006 435/6.16 |
| 2009/0023136 A1 | 1/2009 | Weinshilboum et al. | |
| 2010/0317726 A1 | 12/2010 | Figg et al. | |
| 2011/0110926 A1 | 5/2011 | Luo et al. | |
| 2013/0039908 A1 | 2/2013 | Reed et al. | |
| 2013/0196866 A1 | 8/2013 | Pestano et al. | |
| 2014/0106363 A1 | 4/2014 | Smit | |

FOREIGN PATENT DOCUMENTS

WO   2012033918 A2   3/2012

OTHER PUBLICATIONS

Park et al. Urology. 2007. 70(2): 374-479.*
Chang et al. Cell. Aug. 29, 2013. 154(5): 1074-1084 and "Supplemental Information" and Supplemental Figures.*
Ryan et al Clinical Cancer Research. published online Jul. 15, 2011. 17(14): 4854.*
Pomerantz et a . Clinical Progression to Castration-Recurrent Prostate Cancer in Androgen Action in Prostate Cancer. Springer Science and Business Media, LLC, D.J Tindall and J. Mohler (eds). 2009. p. 59-72.*
deBono et al New England J Med. 2011. 364(21): 1995.*
Goodman, Alice. The ASCO Post. Jun. 15, 2012, pp. 1-2, available via url: <ascopost.com/issues/june-15-2012/encouraging-results-with-neoadjuvant-therapy-for-high-risk-prostate-cancer.aspx>.*
Asai, "Methods in Cell Biology, vol. 37, Antibodies in Cell Biology", pp. 1-4.
Attard, Gerhardt, et al. "Clinical and biochemical consequences of CYP17A1 inhibition with abiraterone given with and without exogenous glucocorticoids in castrate men with advanced prostate cancer." The Journal of Clinical Endocrinology & Metabolism 97.2 (2011): 507-516.
Bloom, Joanna, et al. "Proteasome-mediated degradation of p21 via N-terminal ubiquitinylation." Cell 115.1 (2003): 71-82.
Chang, Kai-Hsiung, and Nima Sharifi. "Prostate cancer—from steroid transformations to clinical translation." Nature Reviews Urology 9.12 (2012): 721-724.
Chang, Kai-Hsiung, et al. "Dihydrotestosterone synthesis bypasses testosterone to drive castration-resistant prostate cancer.". Proceedings of the National Academy of Sciences 108.33 (2011): 13728-13733.
Chapman, Paul B., et al. "Improved survival with vemurafenib in melanoma with BRAF V600E mutation." New England Journal of Medicine 364.26 (2011): 2507-2516.
Cox, Jürgen, and Matthias Mann. "MaxQuant enables high peptide identification rates, individualized ppb-range mass accuracies and proteome-wide protein quantification." Nature biotechnology 26.12 (2008): 1367-1372.
Cunningham, Julie M., et al. "Evaluation of genetic variations in the androgen and estrogen metabolic pathways as risk factors for sporadic and familial prostate cancer." Cancer Epidemiology Biomarkers & Prevention 16.5 (2007): 969-978.
De Bono, Johann S., et al. "Abiraterone and increased survival in metastatic prostate cancer." New England Journal of Medicine 364.21 (2011): 1995-2005.
Feng, Ximao, et al. "Spectroscopic Study of the Light-Harvesting CP29 Antenna Complex of Photosystem I 殷 Part I." The Journal of Physical Chemistry B 117.22 (2013): 6585-6592.
Greenberg, N. M., et al. "Prostate cancer in a transgenic mouse." Proceedings of the National Academy of Sciences 92.8. (1995): 3439-3443.

(Continued)

*Primary Examiner* — Carla Myers
(74) *Attorney, Agent, or Firm* — Tarolli, Sundheim, Covell & Tummino LLP

(57) ABSTRACT

Methods and kits for characterizing a subject having a steroid-dependent disease such as prostate cancer are described. A method of treating a steroid-dependent disease in a subject by obtaining a biological sample from the subject, determining if the HSD3B1(1245C) gene or 3βHSD1(367T) protein is expressed in the biological sample, and providing treatment other than or in addition to steroid ablation to the subject if the HSD3B1(1245C) gene or 3βHSD1(367T) protein is expressed is also described.

11 Claims, 11 Drawing Sheets

(56) References Cited

OTHER PUBLICATIONS

Greenman, Christopher, et al. "Patterns of somatic mutation in human cancer genomes." Nature 446.7132 (2007): 153-158.
Kan, Charlene E., et al. "p53-Mediated Growth Suppression in Response to Nutlin-3 in Cyclin D1—Transformed Cells Occurs Independently of p21." Cancer research 67.20 (2007): 9862-9868.
Kobayashi, Susumu, et al. "EGFR mutation and resistance of non-small-cell lung cancer to gefitinib." New England Journal of Medicine 352.8 (2005): 786-792.
Li, Rui, et al. "Abiraterone inhibits 3β-hydroxysteroid dehydrogenase: a rationale for increasing drug exposure in castration-resistant prostate cancer." Clinical cancer research 18.13 (2012): 3571-3579.
Lorence, Matthew C., et al. "Human 3β-Hydroxysteroid Dehydrogenase/δ5→4Isomerase from Placenta: Expression in Nonsteroidogenic Cells of a Protein that Catalyzes the Dehydrogenation/Isomerization of C21 and C19 Steroids." Endocrinology 126.5 (1990): 2493-2498.
Ong, Shao-En, et al. "Stable isotope labeling by amino acids in cell culture, SILAC, as a simple and accurate approach to expression proteomics." Molecular & cellular proteomics 1.5 (2002): 376-386.
Polin, Lisa, et al. "Treatment of human prostate tumors PC-3 and TSU-PR1 with standard and investigational agents in SCID mice." Investigational new drugs 15.2 (1997): 99-108.
Rodriguez, Manuel S., et al. "SUMO-1 modification activates the transcriptional response of p53." The EMBO journal 18.22 (1999): 6455-6461.
Scher, Howard I., et al. "Increased survival with enzalutamide in prostate cancer after chemotherapy." New England Journal of Medicine 367.13 (2012): 1187-1197.
Sharifi, Nima. "Minireview: androgen metabolism in castration-resistant prostate cancer." Molecular Endocrinology 27.5 (2013): 708-714.
Shimodaira, Masanori, et al. "Association of HSD3B1 and HSD3B2 gene polymorphisms with essential hypertension, aldosterone level and left ventricular structure." European Journal of Endocrinology (2010).
Simard, Jacques, et al. "Molecular biology of the 3β-hydroxysteroid dehydrogenase/Δ5-Δ4 isomerase gene family." Endocrine reviews 26.4 (2005): 525-582.
Song, Bao-Liang, Navdar Sever, and Russell A. DeBose-Boyd. "Gp78, a membrane-anchored ubiquitin ligase, associates with Insig-1 and couples sterol-regulated ubiquitination to degradation of HMG CoA reductase." Molecular cell 19.6 (2005): 829-840.
Stites, et al., "Basic and Clinical Immunology", a LANGE Medical book, seventh edition, pp. 1-4.
Tran, Chris, et al. "Development of a second-generation antiandrogen for treatment of advanced prostate cancer." Science 324.5928 (2009): 787-790.
Wang, Qiuyan, Lianyun Li, and Yihong Ye. "Inhibition of p97-dependent protein degradation by Eeyarestatin I." Journal of Biological Chemistry 283.12 (2008): 7445-7454.
Wang et al., "Human 3β-hydroxysteroid dehydrogenase types 1 and 2: Gene sequence variation and functional genomics", J. Steroid Biochem Mol Biol., Oct. 2007; 107(1-2): 88-99.
Chang et al., "Androgen metabolism in prostate cancer: from molecular mechanisms to clinical consequences", British Journal of Cancer, 2014, 111, pp. 1249-1254.
PCT International Search Report and Written Opinion for PCT/US2014/046477, dated Dec. 10, 2014, pp. 1-12.
Wilson, Elizabeth M. "More evidence intratumoral DHT synthesis drives castration-resistant prostate cancer." Asian journal of andrology 16.1 (2014): 99.
Chang, Bao-li, et al. "Joint effect of HSD3B1 and HSD3B2 genes is associated with hereditary and sporadic prostate cancer susceptibility." Cancer Research 62.6 (2002): 1784-1789.
JP Office Action for corresponding JP PCT 2016/527004, dated Oct. 25, 2016, pp. 1-7.
Chang, Boa-li, et al. "Joint effect of HSD3B1 and HSD3B2 genes is associated with hereditary and sporadic prostate cancer susceptibility." Cancer Research 62.6 (2002): 1784-1789.
Chang, Boa-li, et al. "A Gain-of-Function Mutation in DHT Synthesis in Castration-Resistant Prostate Cancer," Cell 154, 1074-1084, Aug. 29, 2013.
Wilson, Elizabeth M. "More evidence intratumoral DHT synthesis drives castration-resistant prostate cancer," Asian Journal of Andrology (2014) 16, (99-100). Dec. 16, 2013.
Shapiro, D., et al. "Current and emerging treatments in the Management of Castration-Resistant Prostate Cancer." Expert Rev. Anticancer Ther. 2012; 12(7): 951-964.
Supplementary search report corresponding to European Patent App. No. EP14826459.1, dated Apr. 18, 2017, 19 pages.
Office Action for corresponding JP Appl. No. 2016-527004, dated Apr. 25, 2017, 4 pages.

* cited by examiner

```
                              SEQUENCE LISTING

<160> NUMBER OF SEQ ID NOS: 27

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggaccggcac aaggagaacc tgaagtccaa gactcag                              37

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctgagtcttg gacttcaggt tctccttgtg ccggtcc                              37

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tccgcggccg cggagtgatt cctgcta                                        27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aagacgcgtg agctctagta gtcaaaa                                        27

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atgtggaggg aggtgtgagt                                                20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 6
acggagatgg gtctcttcca                                                      20

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
actgaattcc aggccaattt acacctatcg                                           30

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
actctcgagt caaactatgt gaaggaatgg a                                         31

<210> SEQ ID NO 9
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tgctgttgac agtgagcgac ctcatacaga aagtgacaag tagtgaagcc acagatgtac          60
ttgtcacttt ctgtatgagg ctgcctactg cctcgga                                  97

<210> SEQ ID NO 10
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tgctgttgac agtgagcgaa gaggaaagac catgtggttt tagtgaagcc acagatgtaa          60
aaccacatgg tctttcctct gtgcctactg cctcgga                                  97

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccatgtggtt tgctgttacc aa                                                  22

<210> SEQ ID NO 12
<211> LENGTH: 25
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 12
tcaaaacgac cctcaagtta aaaga                                         25

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcatgggatg gggatgaagt aag                                           23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
catcaaatct gagggttgtc tgga                                          24

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccatttgcag gatctgtctg                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggatgtgtct tggggagcaa                                               20

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgagggcacc tggaaaac                                                 18

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic

```
                                  primer

<400> SEQUENCE: 18
cacattcccc cggatatga                                                    19

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agaaggctgg ggctcatttg                                                   20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aggggccatc cacagtcttc                                                   20

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 21

His His His His His His
1               5

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gatgagccat tcctgaggag agcctgccag gac                                    33

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtcctggcag gctctcctca ggaatggctc atc                                    33

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
```

```
          primer

<400> SEQUENCE: 24
gaggaagcca agcagagaac ggtggagtgg gtt                                33

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aacccactcc accgttctct gcttggcttc ctc                                33

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Thr Val Leu Glu Gly Asp Ile Leu Asp Glu Pro Phe Leu Lys Arg
1               5                   10                  15

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Lys Thr Val Glu Trp Val Gly Ser Lys Val Asp Arg
1               5                   10
```

METHOD FOR TREATING CASTRATION-RESISTANT PROSTATE CANCER

CROSS-REFERENCE TO RELATED APPLICATIONS

This application claims priority to U.S. Provisional Patent Application No. 61/846,344, filed on Jul. 15, 2013 which is hereby incorporated by reference in its entirety.

GOVERNMENT FUNDING

The present invention was made with government support under CA172382 awarded by the National Institutes of Health The U.S. Government has certain rights in this invention.

SEQUENCE LISTING

The instant application contains a Sequence Listing which has been submitted electronically in ASCII format and is hereby incorporated by reference in its entirety. Said ASCII copy, created on Jul. 2, 2014, is named CCF-022549USORD_SL.txt and is 6,623 bytes in size.

BACKGROUND

The growth of cancerous prostate cells requires stimulation of the androgen receptor (AR) by androgens, the most potent of which is dihydrotestosterone (DHT). Advanced prostate cancer usually initially regresses with gonadal testosterone deprivation therapy (i.e., medical or surgical castration), but it almost always eventually progresses as castration-resistant prostate cancer (CRPC). The CRPC phenotype is driven by a gain-of-function in the androgen receptor (AR) that is usually accompanied by intratumoral DHT concentrations of about 1 nM, which is sufficient to drive expression of AR-induced genes, including the TMPRSS2-ETS fusion oncogene. Sharifi, N., Mol Endocrinol 27, 708-714 (2013). The requirement for intratumoral androgen synthesis in driving CRPC progression is most clearly demonstrated by the survival benefit conferred by abiraterone acetate, a drug which blocks androgen synthesis by inhibiting 17α-hydroxylase/17,20-lyase (CYP17A1), and enzalutamide, a potent AR antagonist that blocks DHT access to the AR ligand-binding domain. de Bono et al., N Engl J Med 364, 1995-2005 (2011); Scher et al., N Engl J Med. 367, 1187-97 (2012).

Intratumoral synthesis of DHT from precursors that are secreted from the adrenal gland occurs through a pathway that circumvents testosterone. Chang et al., Proc Natl Acad Sci USA 108, 13728-13733 (2011). This synthesis requires three enzymes: 3β-hydroxysteroid dehydrogenase (3βHSD; encoded by HSD3B), steroid-5α-reductase (SRD5A) and 17β-hydroxysteroid dehydrogenase (17βHSD) isoenzymes (see FIG. 1A). Nonetheless, increased DHT synthesis in CRPC has not yet been ascribed to any mutations in genes encoding components of the steroidogenic machinery. 3βHSD oxidizes 3β-hydroxyl to 3-keto and isomerizes $\Delta^5$ to $\Delta^4$ (see FIG. 1A), reactions that together make this step practically irreversible by an enzyme that is required for all possible pathways that lead to the synthesis of DHT. Evaul et al., Endocrinology 151, 3514-3520 (2010). HSD3B1 encodes for the peripherally expressed isoenzyme (3βHSD1) and has a germline single nucleotide polymorphism (SNP) at position 1245 of HSD3B1, converting A→C, which exchanges an asparagine (N) for a threonine (T) at 3βHSD1 amino acid position 367.

The past decade has brought to the fore the development of molecularly targeted therapies that are matched to specific disease-driving enzyme mutations present in a given patient. These advances come mainly in the form of tyrosine kinase inhibitors that target gain-of-function mutations in these signaling enzymes. These include the examples of EGF receptor inhibitors matched with tumors harboring mutant EGF receptor in non-small cell lung cancer and BRAF inhibitors for melanomas that are driven by BRAF mutations Chapman et al. N Engl J Med 364, 2507-2516 (2011); Kobayashi et al., N Engl J Med 352, 786-792 (2005). In contrast, no examples of drug targeting based on enzyme mutations exist in the standard of care for metastatic CRPC.

SUMMARY OF THE INVENTION

Growth of prostate cancer cells is dependent upon androgen stimulation of the androgen receptor (AR). Dihydrotestosterone (DHT), the most potent androgen, is usually synthesized in the prostate from testosterone secreted by the testis. Following chemical or surgical castration, prostate cancers usually shrink owing to testosterone deprivation. However, tumors often recur, forming castration-resistant prostate cancer (CRPC). Here, the inventors show that CRPC sometimes expresses a gain-of-stability mutation leading to a gain-of-function in 3β-hydroxysteroid dehydrogenase type 1 (3βHSD1), which catalyzes the initial rate-limiting step in the conversion of the adrenal-derived steroid dehydroepiandrosterone to DHT. The mutation (N367T) does not affect catalytic function, but it renders the enzyme resistant to ubiquitination and degradation, leading to profound accumulation. Whereas dehydroepiandrosterone conversion to DHT is usually very limited, expression of 367T accelerates this conversion and provides the DHT necessary to activate the AR. The inventors hypothesized that 3βHSD1 is a valid target for the treatment of CRPC.

BRIEF DESCRIPTION OF THE FIGURES

The present invention may be more readily understood by reference to the following figures, wherein.

(367T) is associated with increased protein quantity. Error bars in A, B and D represent the SD from experiments performed in triplicate.

Figure 2:
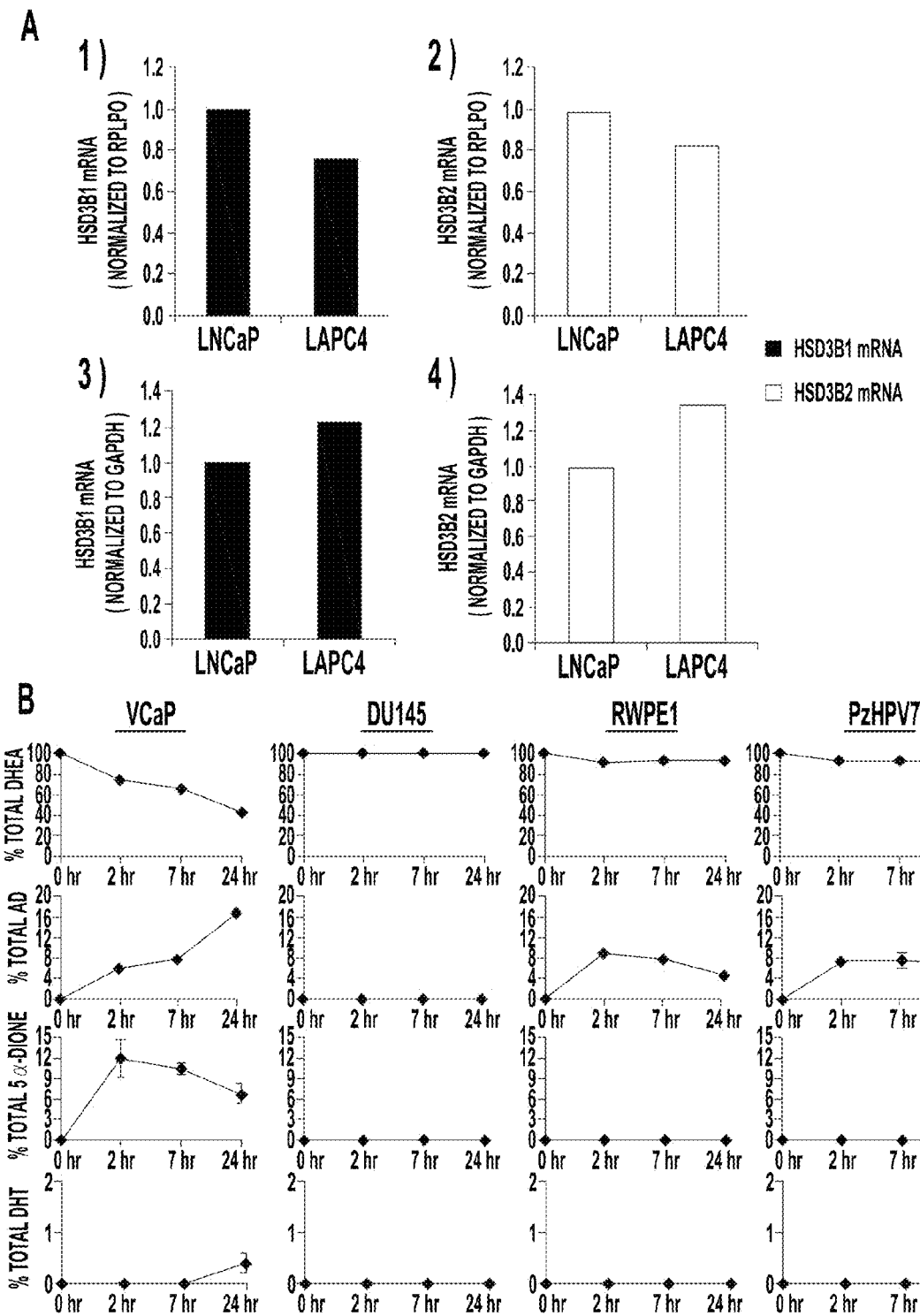

FIG. 2 provides graphs showing the increased metabolic flux from DHEA to AD associated with a point mutation is not attributable to transcriptional regulation and association of flux with the mutant occurs in other models. A. Expression of HSD3B1 and HSD3B2 transcripts are comparable between LNCaP and LAPC4. Expression of HSD3B1 (blue bars) and HSD3B2 (green bars) isoenzymes by qPCR are shown in LAPC4 relative to LNCaP and normalized to RPLP0 (above) and GAPDH (below). Error bars represent the SD from experiments performed in triplicate. B. Metabolic flux from [$^3$H]-DHEA (100 nM) to AD is robust in VCaP with 3βHSD1(367T) and limited with DU145, RWPE-1 and PzHPV7 with 3βHSD1(367N). Downstream flux to 5α-dione and DHT occurs in VCaP and is not detectable in DU145, RWPE-1 and PzHPV7. Steroids were quantitated at the designated time points by HPLC. Experiments were performed in triplicate, and error bars represent the SD.

Figure 3:
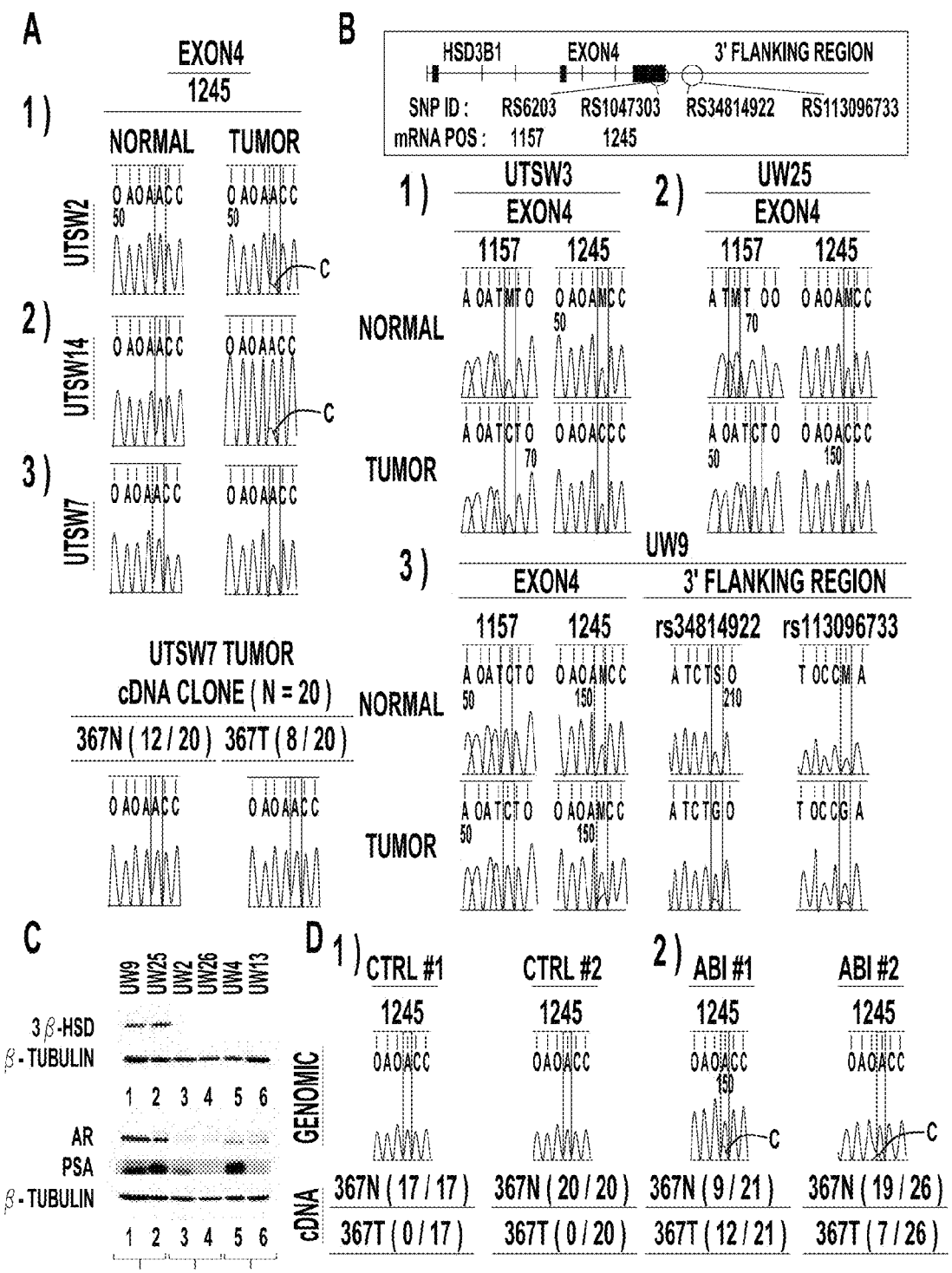

FIG. 3 provides graphs showing that the somatic selection for HSD3B1(1245C) encoding 3βHSD1(367T) occurs with resistance to androgen deprivation. (A) Conversion from A→C in HSD3B1 occurs in 3 CRPC tumors from patients with homozygous wild-type inheritance. Sequence of cDNA clones from a fresh-frozen tumor (UTSW7) confirms expression of HSD3B1(1245C) transcript. (B) Three CRPC tumors from patients with heterozygous inheritance exhibit LOH of the wild-type HSD3B1(1245A) allele. Sequencing informative (heterozygous) adjacent 5' (rs6203) and 3' (rs34814922 and rs113096733) SNPs confirms LOH. (C) 3βHSD1 protein is abundant in tumors with LOH of the HSD3B1(1245A) allele but not tumors with heterozygous expression or homozygous HSD3B1(1245A) expression. Both tumors with LOH tested also express AR and PSA (20 µg protein loaded per lane for each tumor). (D) Somatic mutation converting A→C in HSD3B1 occurs in two LAPC4 xenograft tumors treated with abiraterone acetate (Abi) after orchiectomy and expression of HSD3B1(1245C) transcript encoding 3βHSD1(367T) is evidenced by sequencing cDNA clones from these tumors. Genomic sequence from two representative control tumors (CTRL#1 and CTRL#2) treated with orchiectomy alone is shown for comparison. All 37 cDNA clones from CTRL#1 and CTRL#2 have HSD3B1(1245A) transcript encoding 3βHSD1(367N).

Figure 4:
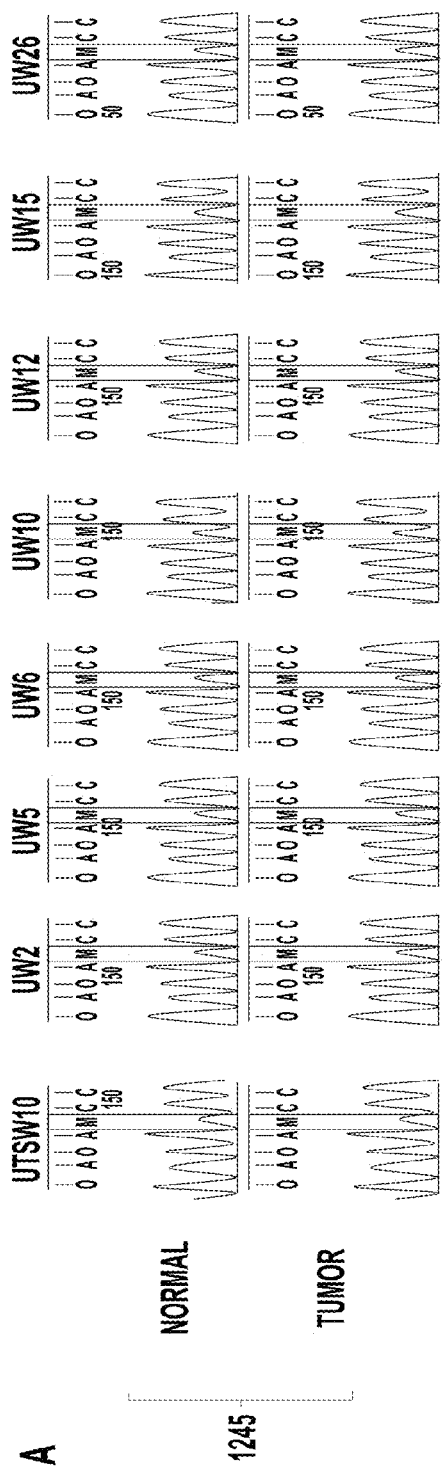

FIG. 4 provides graphs showing the HSD3B1 LOH in human CRPC tissues. A. LOH of the HSD3B1(1245C) allele encoding 3βHSD1(367T) does not occur in CRPC. Shown are the remaining cases with germline heterozygosity not shown in FIG. 3B. These 8 cases maintain both alleles in genomic DNA extracted from CRPC tumors. B. HSD3B1 mRNA expression in UW tumors with LOH does not explain elevated 3βHSD1 protein expression. Expression is normalized to RPLP0 and error bars represent the SD from experiments performed in triplicate.

Figure 5:
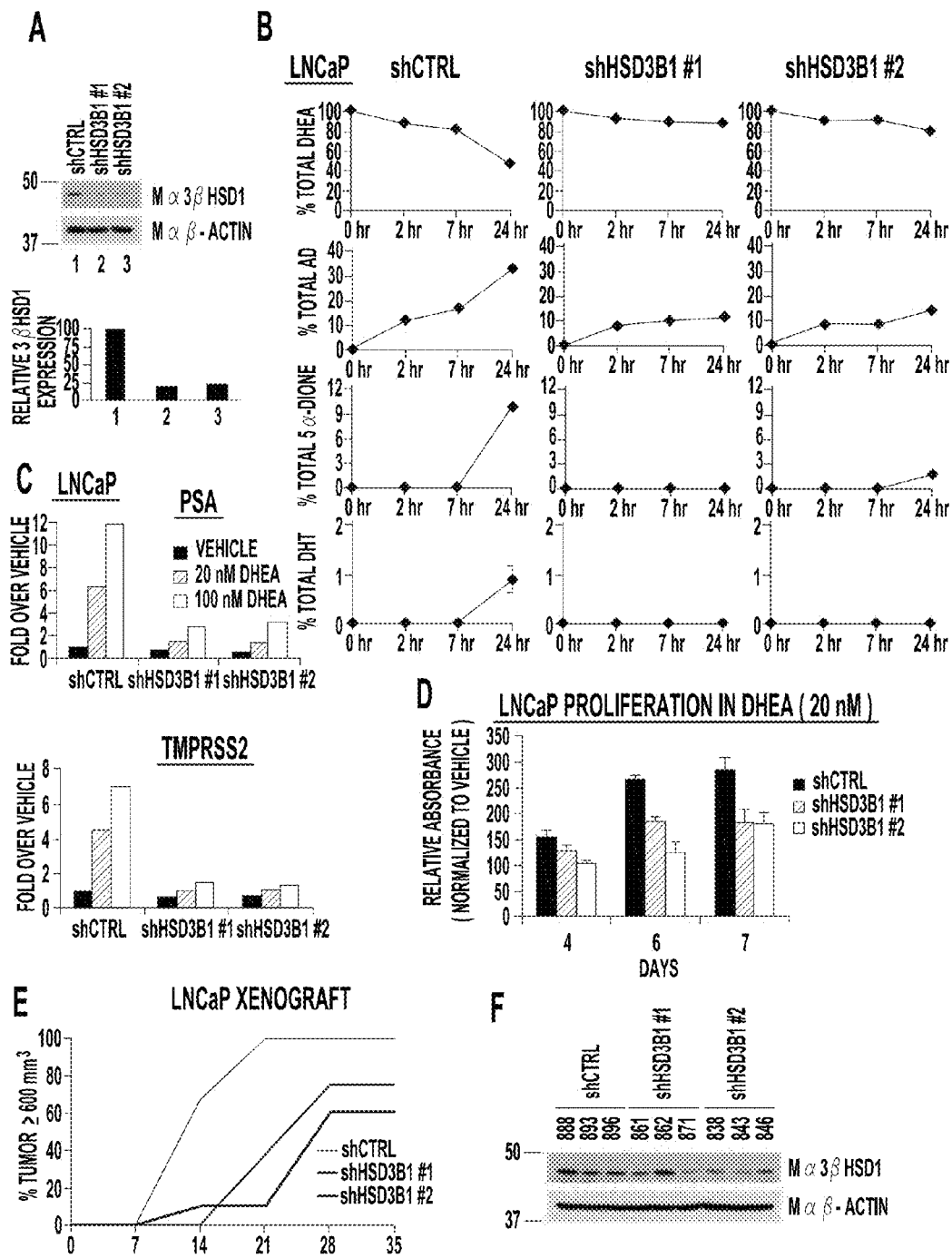

FIG. 5 provides graphs showing that the genetic silencing of 3βHSD1(367T) impedes conversion of DHEA to DHT, induction of PSA and TMPRSS2 expression, and CRPC growth. (A) Stable lentiviral expression of two independent shRNA constructs against HSD3B1 (shHSD3B1 #1 and shHSD3B1 #2) silences 3βHSD1 protein expression in LNCaP. The 3βHSD1 protein was quantitated and normalized to cells expressing nonsilencing lentiviral vector (shCTRL) and β-actin. (B) Silencing 3βHSD1(367T) blocks flux from [$^3$H]-DHEA (100 nM) to AD as well as further downstream conversion to 5α-dione and DHT. Cells were treated with [$^3$H]-DHEA in triplicate and steroids were quantitated with HPLC at the designated time points. (C) Inhibition of AR-regulated genes. Cells were treated with the indicated concentration of DHEA for 24 hours, and gene expression was assessed by qPCR and normalized to shCTRL-infected cells treated with vehicle and the RPLP0 housekeeping gene. (D) Silencing 3βHSD1(367T) inhibits in vitro growth. Cells were grown in the presence of 20 nM DHEA or vehicle and growth for each cell line is normalized to vehicle for each designated day. (E) 3βHSD1(367T) depletion blocks CRPC growth in LNCaP xenografts. Mice underwent surgical orchiectomy and DHEA pellet implantation concomitantly when xenograft tumors reached a threshold volume of 100 mm$^3$. Fifteen mice were initiated in each cohort, 7, 8 and 10 mice in shCTRL, shHSD3B1 #1, and shHSD3B1 #2 groups, respectively, achieved a tumor volume of 100 mm$^3$ in eugonadal mice, underwent orchiectomy and were included in the CRPC analysis. The number of days from orchiectomy to tumor volume ≥600 mm$^3$ is shown. In the comparisons of shCTRL vs shHSD3B1 #1 and shHSD3B1 #2, P=0.002 and 0.003, respectively, using a log rank test. (F) 3βHSD1(367T) protein is regained in CRPC tumors that grow from LNCaP expressing shHSD3B1 #1 and shHSD3B1 #2. Immunoblot for 3βHSD1 and β-actin were performed on protein from the indicated LNCaP CRPC tumors. Error bars in B, C and D represent the SD for experiments performed in triplicate.

Figure 6:
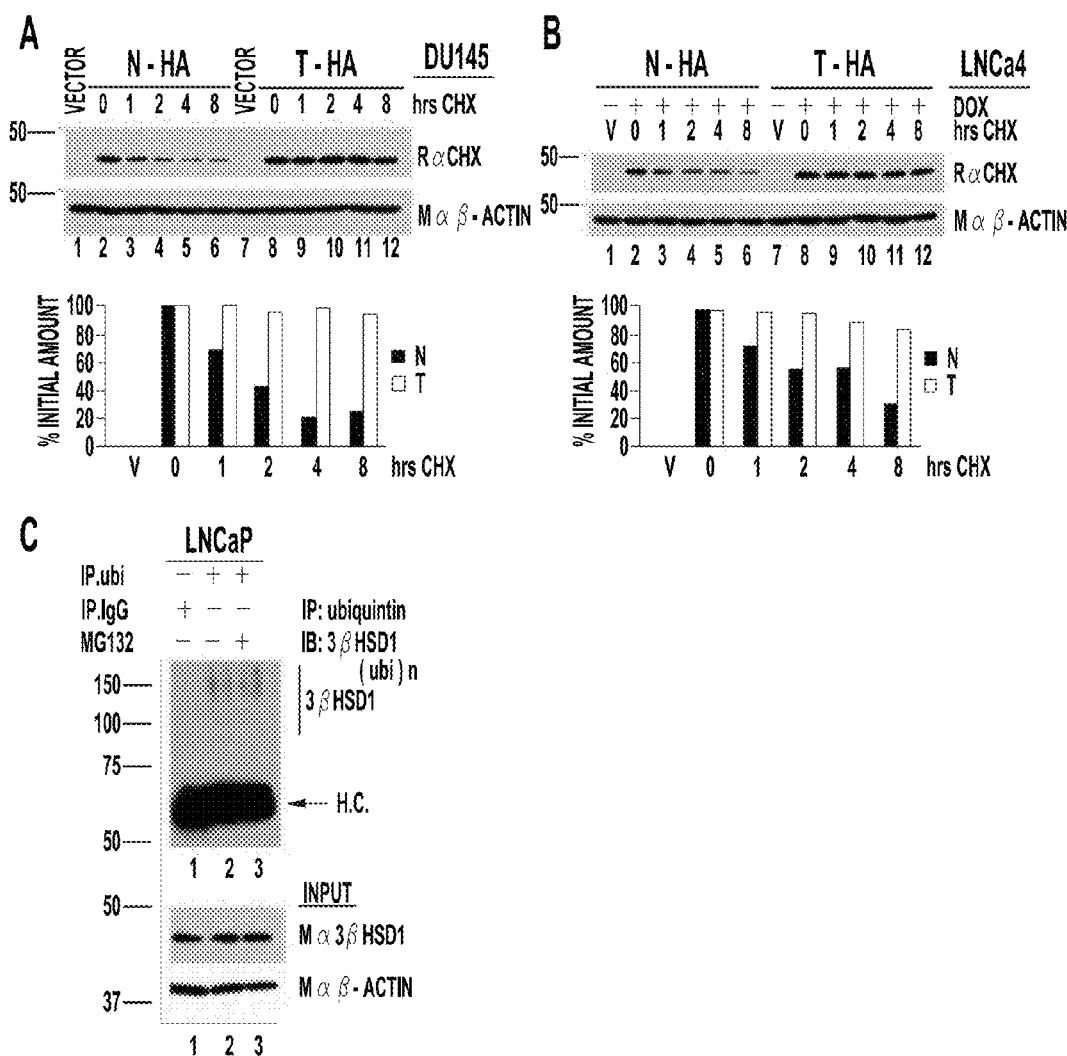

FIG. 6 provides graphs and images showing the protein half-life of 3βHSD1(367T) and 3βHSD1(367N). A. HA-tagged 3βHSD1(367T) (T-HA) has a prolonged half-life compared to wild-type 3βHSD1(367N) (N-HA) protein in the DU145 prostate cancer cell line. Cells were transiently transfected with empty vector alone (vector), constructs encoding for wild-type (N-HA) and mutant (T-HA) protein and treated with CHX, protein was collected at the designated time points, Western blot was performed and signal was quantitated and normalized to time zero and β-actin. The calculated half-lives of 3βHSD1(367N) and 3βHSD1 (367T) proteins are 2.7 and >100 hours, respectively. B. Stable expression in LAPC4 demonstrates a longer half-life of HA-tagged 3βHSD1(367T) (T-HA) compared to 3βHSD1(367N) (N-HA) protein. Expression was induced after lentiviral infection with a doxycycline-inducible expression construct or vehicle (v). Cells were treated with CHX, protein was collected at the time points indicated, Western blot was performed, and signal was quantitated and normalized to time zero and β-actin. The calculated half-lives of wild-type and mutant proteins are 3.7 and >100 hours, respectively. C. Proteosome inhibition with MG132 (10 uM; 8 hours) results in no increase in polyubiquitinated 3βHSD1(367T) protein in LNCaP as evidenced by immunoprecipitation with an anti-ubiquitin antibody.

Figure 7:
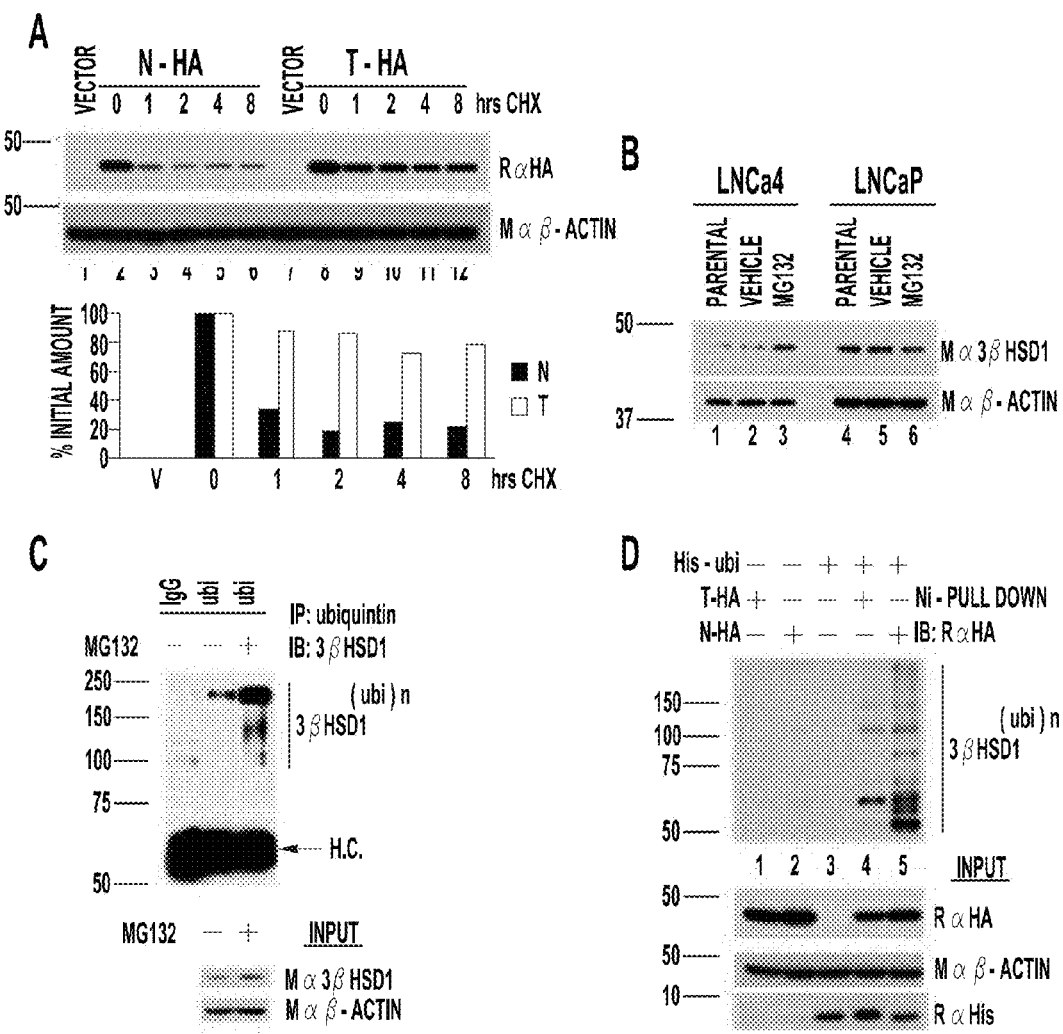

FIG. 7 provides blot images showing that the resistance to ubiquitination and proteosome-mediated degradation occurs with 3βHSD1(367T) which results in prolonged protein half-life. (A) 3βHSD1(367T) persists after inhibition of protein translation. LAPC4 cells were transiently transfected with constructs encoding for wild-type (N-HA) and (T-HA) protein and treated with cycloheximide (CHX) for the designated incubation times. Western blot with anti-HA antibody was performed, and signal was quantitated and normalized to time zero and β-actin. (B) Treatment with MG132 (10 µM; 8 hours) reverses 3βHSD1(367N) protein loss in LAPC4 and results in no 3βHSD1(367T) protein increase in LNCaP. (C) Proteosome inhibition with MG132 (10 µM; 8 hours) results in an increase in polyubiquitinated 3βHSD1(367N) protein in LAPC4 as evidenced by immunoprecipitation with an anti-ubiquitin antibody. (D) Loss of 3βHSD1(367T) vulnerability to proteosome-mediated degradation is explained by diminished susceptibility to ubiquitination. His-ubiquitin (His-ubi) was expressed with wild-type (N-HA) or (T-HA) protein in 293 cells, followed by pull down with Ni-agarose beads and anti-HA immunoblot.

Figure 8:
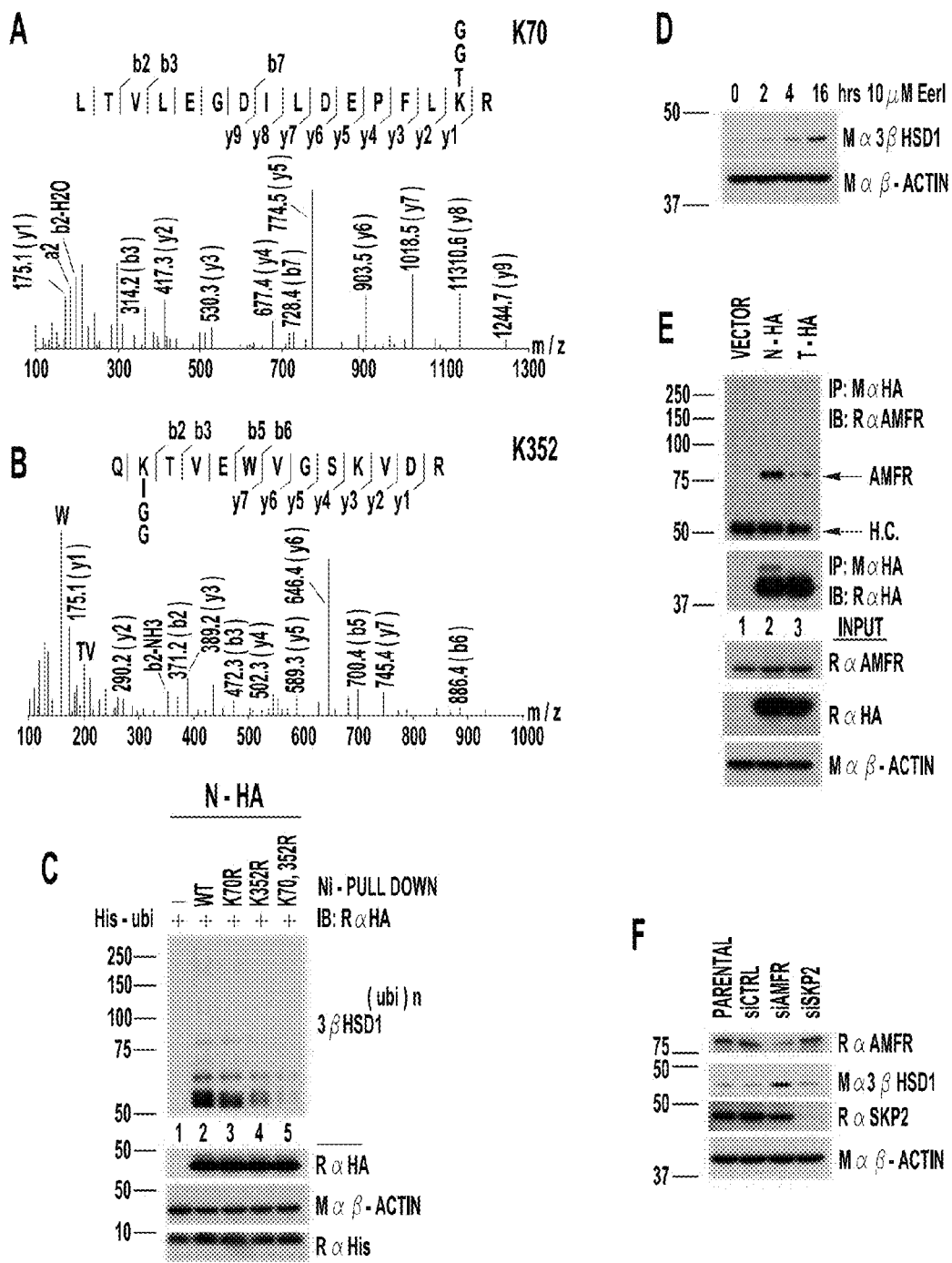

FIG. 8 provides mass spectroscopy results and blot images showing that the ER-associated degradation (ERAD) pathway and AFMR regulate 3βHSD1 ubiquitination and degradation. (A, B) K70 and K352 ubiquitination on 3βHSD1(367N) is detectable by mass spectrometry. FIGS. 8A and 8B disclose the core peptide sequences as SEQ ID NOS 26-27, respectively, in order of appearance. (C) K70, 352R mutant 3βHSD1(367N) is resistant to ubiquitination. K70R and K352R single and double mutant forms of N-HA were expressed with His-ubi in 293 cells, followed by pull down with Ni-agarose beads and anti-HA immunoblot. (D) Treatment with the ERAD inhibitor, Eeyarestatin I (EerI, 10 µM), increases endogenous 3βHSD1 protein in LAPC4. (E) AMFR preferentially physically associates with wild-type protein (N-HA). Proteins were expressed in 293 cells, immunoprecipitated with anti-HA antibody, followed by immunoblot for AMFR. (F) Silencing the ubiquitin E3-ligase AMFR increases 3βHSD1 protein detected in LAPC4 cells. In contrast, genetically silencing the ubiquitin E3-ligase SKP2 has no detectable effect on 3βHSD1.

Figure 9:
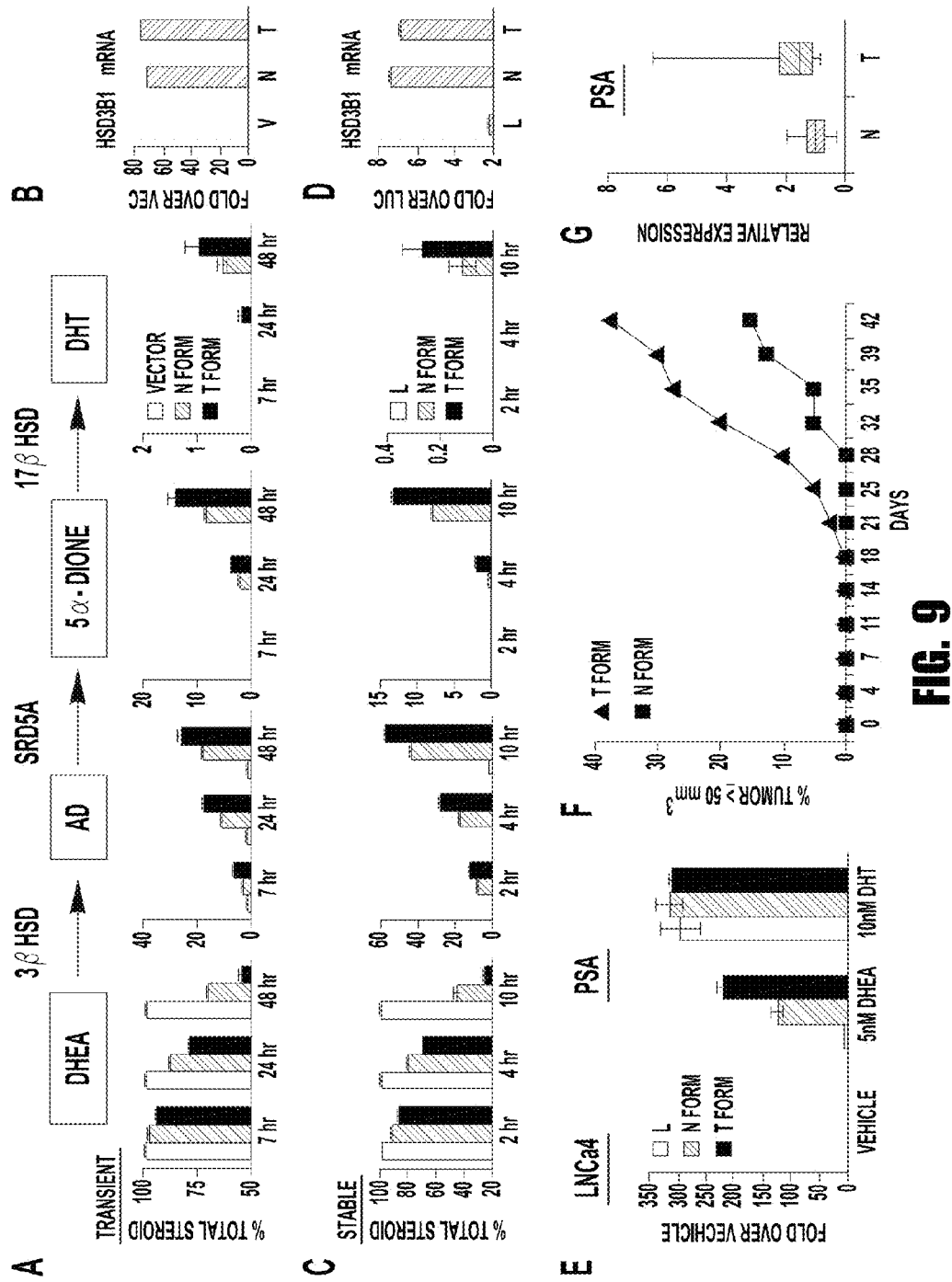

FIG. 9 provides graphs showing that 3βHSD1(367T) increases metabolic flux from DHEA to DHT and elicits CRPC. (A) Transient expression of 3βHSD1(367T) (T, blue bars) leads to increased conversion from DHEA to AD and downstream steroids compared with 3βHSD1(367N) (N, red bars). LAPC4 cells were transfected with the indicated plasmid, treated with CHX, and cultured with [$^3$H]-DHEA (100 nM); steroids were extracted and measured by HPLC at the designated time points (p-value=0.023 for the difference in DHT synthesis by the N and T forms using by Student's t-test). (B) Transient transfection results in equivalent expression of both transcripts by qPCR. (C) Stable expression demonstrates increased activity of 3βHSD1 (367T). Lentiviral constructs expressing luciferase (L), wild-type (N), or (T), were stably expressed (without CHX treatment) and flux from [$^3$H]-DHEA to DHT was assessed, as described previously (p-value=0.015 for the difference in DHT synthesis by the N and T forms using Student's t-test). (D) Expression of both enzyme transcripts by qPCR is comparable. (E) Increased flux from DHEA to DHT with stable expression of 3βHSD1(367T) leads to amplified expression of PSA in LAPC4. Cells stably expressing the designated constructs were treated with the indicated steroids for 48 hours. PSA expression induced by the DHT positive control is equivalent among the three cell populations. For B, D and E, expression is normalized to RPLP0 and vector, luciferase, or vehicle controls. Error bars represent the SD for experiments performed in triplicate. (F) Development of CRPC occurs more rapidly in LAPC4 xenografts stably expressing 3βHSD1(367T) as compared with 3βHSD1(367N). Time from subcutaneous injection of cells in each flank to tumor size=50 mm$^3$ is shown for each tumor that developed in a mouse flank (n=40 mouse flanks in each group). P=0.017 for the comparison using a log rank test. (G) PSA expression is higher in CRPC tumors expressing 3βHSD1(367T) compared with 3βHSD1(367N) (p-value=0.015 by Student's t-test). Expression is normalized to RPLP0. Bars represent the upper and lower quartiles of individual tumor values.

Figure 10:
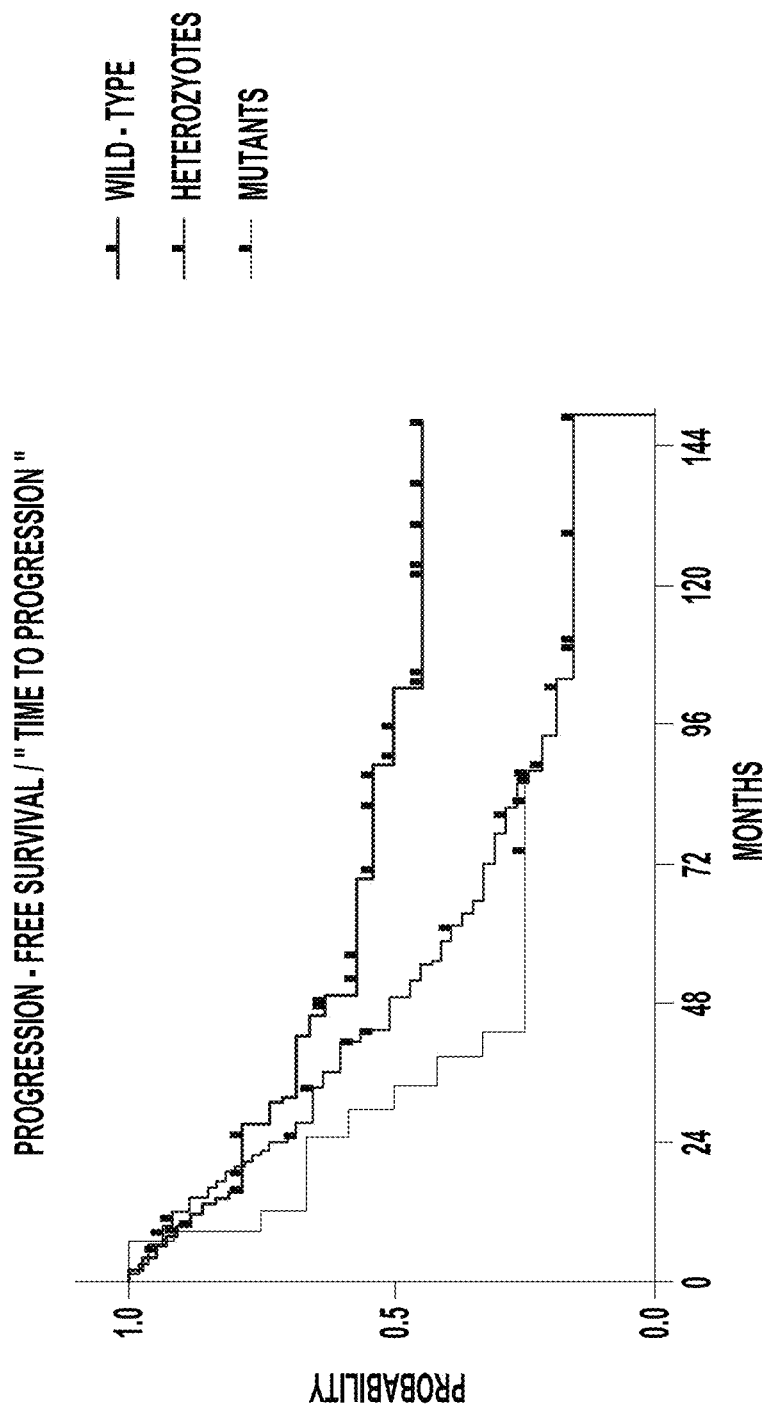

FIG. 10 provides a graph showing the effect of the presence of the HSD3B1 mutation on time to progression (TTP) in patients treated with standard androgen deprivation therapy (ADT). The results show a strong correlation between the HSD3B1 variant and time to progression on ADT. Homozygous-variant men have a markedly shorter time to progression compared to men who are homozygous wild-type (31.8 months vs. 78.9 months), whereas heterozygotes have an intermediate clinical course (time to progression=49.7 months). In both cases the log-rank p value<0.05 when compared to the reference group (homozygous wild-type), and there is evidence of a gene-dosage effect (log-rank test for trend, p=0.011)

Figure 11:
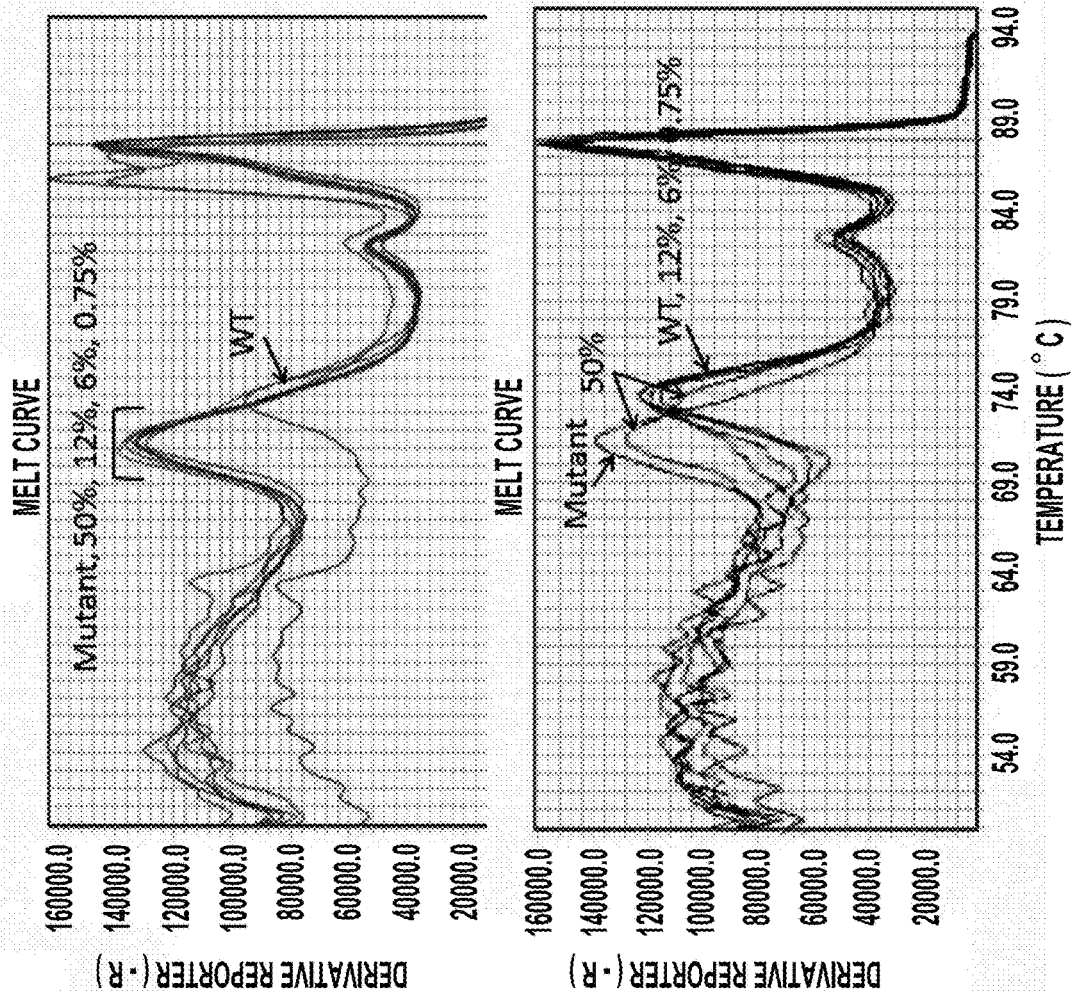

FIG. 11 provides graphs showing the melt curves for a somatic mutation detection method (PCR1) and a germline SNP detection method (PCR2). The differences in melt temperature can be used to detect the presence of HSD3B1 (1245C).

DETAILED DESCRIPTION OF THE INVENTION

The present invention relates to a gain-of-function in HSD3B1 that increases DHT synthesis, eliciting resistance to androgen deprivation therapy in steroid-dependent diseases such as prostate cancer. Detection of this gain of function can be used to guide treatment of steroid-dependent diseases.

Definitions

As used herein, the term "diagnosis" can encompass determining the likelihood that a subject will develop a disease, or the existence or nature of disease in a subject. The term diagnosis, as used herein also encompasses determining the severity and probable outcome of disease or episode of disease or prospect of recovery, which is generally referred to as prognosis). "Diagnosis" can also encompass diagnosis in the context of rational therapy, in which the diagnosis guides therapy, including initial selection of therapy, modification of therapy (e.g., adjustment of dose or dosage regimen), and the like.

As used herein, the term "prognosis" refers to a prediction of the probable course and outcome of a disease, or the likelihood of recovery from a disease. Prognosis is distinguished from diagnosis in that it is generally already known that the subject has the disease, although prognosis and diagnosis can be carried out simultaneously. In the case of a prognosis for prostate cancer, the prognosis categorizes the relative severity of the prostate cancer, which can be used to guide selection of appropriate therapy for the prostate cancer.

As used herein, the terms "treatment," "treating," and the like, refer to obtaining a desired pharmacologic or physiologic effect. The effect may be therapeutic in terms of a partial or complete cure for a disease or an adverse effect attributable to the disease. "Treatment," as used herein, covers any treatment of a disease in a mammal, particularly in a human, and can include inhibiting the disease or condition, i.e., arresting its development; and relieving the disease, i.e., causing regression of the disease.

Prevention or prophylaxis, as used herein, refers to preventing the disease or a symptom of a disease from occurring in a subject which may be predisposed to the disease but has not yet been diagnosed as having it (e.g., including diseases that may be associated with or caused by a primary disease). Prevention may include completely or partially preventing a disease or symptom.

The term therapy, as used herein, encompasses activity carried out to treat a disease. The specific activity carried out to conduct therapy can include use of surgery, radiotherapy, hormonal therapy, chemotherapy, or the use of one or more therapeutic agents (e.g., anticancer agents).

The terms "therapeutically effective" and "pharmacologically effective" are intended to qualify the amount of an agent which will achieve the goal of improvement in disease severity and the frequency of incidence over treatment of each agent by itself, while avoiding adverse side effects typically associated with alternative therapies. The effectiveness of treatment may be measured by evaluating a reduction in tumor load or decrease in tumor growth in a subject in response to the administration of anticancer agents. The reduction in tumor load may be represent a direct decrease in mass, or it may be measured in terms of tumor growth delay, which is calculated by subtracting the average time for control tumors to grow over to a certain volume from the time required for treated tumors to grow to the same volume.

The term "genotype" refers to the alleles present in DNA from a subject or patient, where an allele can be defined by the particular nucleotide(s) present in a nucleic acid sequence at a particular site(s). Often a genotype is the nucleotide(s) present at a single polymorphic site known to vary in the human population.

Furthermore, a genotype or polymorphic variant may be expressed in terms of a "haplotype," which as used herein refers to two or more polymorphic variants occurring within genomic DNA in a group of subjects within a population. For example, two SNPs may exist within a gene where each SNP position includes a cytosine variation and an adenine variation. Certain subjects in a population may carry one allele (heterozygous) or two alleles (homozygous) having the gene with a cytosine at each SNP position. As the two cytosines corresponding to each SNP in the gene travel together on one or both alleles in these subjects, the subjects can be characterized as having a cytosine/cytosine haplotype with respect to the two SNPs in the gene.

As used herein, the term "polymorphic site" refers to a region in a nucleic acid at which two or more alternative nucleotide sequences are observed in a significant number of nucleic acid samples from a population of subjects. A polymorphic site may be a nucleotide sequence of two or more nucleotides, an inserted nucleotide or nucleotide sequence, a deleted nucleotide or nucleotide sequence, or a microsatellite, for example. A polymorphic site may be two or more nucleotides in length, may be 3, 4, 5, 6, 7, 8, 9, 10, 11, 12, 13, 14, 15 or more, 20 or more, 30 or more, 50 or more, 75 or more, 100 or more, 500 or more, or about 1000 nucleotides in length, where all or some of the nucleotide sequences differ within the region. A polymorphic site is often one nucleotide in length, which is referred to herein as a single nucleotide polymorphism (SNP).

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs.

As used herein and in the appended claims, the singular forms "a", "and", and "the" include plural referents unless the context clearly dictates otherwise. Thus, for example, reference to "a sample" also includes a plurality of such samples and reference to "the 3βHSD1(367T) protein" includes reference to one or more protein molecules, and so forth.

One aspect of the invention provides a method of diagnosing a subject having a steroid-dependent disease, including the steps of obtaining a biological sample from the subject, determining if the HSD3B1(1245C) gene or 3βHSD1(367T) protein is expressed in the biological sample, and diagnosing the subject as being resistant to steroid ablation if the HSD3B1(1245C) gene or 3βHSD1 (367T) protein is expressed.

Another aspect of the invention provides a method of treating a steroid-dependent disease in a subject in need thereof that includes the steps of obtaining a biological sample from the subject, determining if the HSD3B1 (1245C) gene or 3βHSD1(367T) protein is expressed in the biological sample, and providing treatment other than or in addition to steroid ablation to the subject if the HSD3B1 (1245C) gene or 3βHSD1(367T) protein is expressed.

Steroid-Dependent Disease

The present invention provides methods for diagnosing, treating, and guiding treatment of steroid-dependent disease. Steroid-dependent disease, as used herein, refers to diseases that depend on the presence of steroid hormones in order to persist. In particular, steroid-dependent diseases refer to diseases in which 3β-hydroxysteroid dehydrogenase (3βHSD; encoded by HSD3B plays a role in regulating the amount of steroid upon which the disease depends. Examples of steroid-dependent diseases include asthma, hypertension, inflammatory bowel disease (e.g., Crohn's disease and ulcerative colitis), nephritic syndrome, endometriosis, breast cancer, and prostate cancer. As used herein, steroid-dependent disease also encompasses a disease which is normally characterized as being a steroid-dependent disease, but which has or develops steroid independence.

In some embodiments, the steroid-dependent disease is cancer. Examples of steroid-dependent cancer include bladder cancer, breast cancer, endometrial cancer, pancreatic cancer, and prostate cancer. The identification of additional types of cancer which can be steroid-dependent is ongoing. In some embodiments, the steroid upon which the cancer depends is a sex steroid. Sex steroids, also known as gonadal steroids, are steroid hormones that interact with androgen or estrogen receptors. Sex steroids include androgens such as anabolic steroids, androstenedione, dehydroepiandrosterone, dihydrotestosterone, and testosterone; estrogens such as estradiol, estriol, and estrone; and the progestogen progesterone.

As used herein, the terms "tumor" or "cancer" refer to a condition characterized by anomalous rapid proliferation of abnormal cells of a subject. The abnormal cells often are referred to as "neoplastic cells," which are transformed cells that can form a solid tumor. The term "tumor" refers to an abnormal mass or population of cells (e.g., two or more cells) that result from excessive or abnormal cell division, whether malignant or benign, and pre-cancerous and cancerous cells. Malignant tumors are distinguished from benign growths or tumors in that, in addition to uncontrolled cellular proliferation, they can invade surrounding tissues and can metastasize.

In some embodiments, the cancer is prostate cancer. Prostate cancer, as used herein, refers to a disease in which cancer develops in the prostate gland of the male reproductive system. Prostate cancer is classified as an adenocarcinoma, or glandular cancer, that begins when normal semen-secreting prostate gland cells mutate into cancer cells. In the initial stage of prostate cancer, small clumps of cancer cells remain confined to otherwise normal prostate glands, a condition known as carcinoma in situ or prostatic intraepithelial neoplasia (PIN), a prostate precancer. Over time these cancer cells begin to multiply and spread to the surrounding prostate tissue (the stroma), forming a tumor. While prostate cancer originates and may remain in the prostate, prostate tumor cells may develop the ability to travel in the bloodstream and lymphatic system and thus be found in other organs or tissues. Prostate cancer most commonly metastasizes to the bones, lymph nodes, rectum, and bladder. Treatment or prevention of prostate cancer, as used herein, also refers to the treatment of metastasized prostate cancer found in other organs or tissues.

Most steroid-dependent cancers become refractory after one to three years and resume growth despite therapy. Accordingly, in some embodiments, the prostate cancer is castration-resistant prostate cancer, which is also known as hormone-refractory prostate cancer or androgen-independent prostate cancer. Subjects who have castration-resistant prostate cancer are no longer responsive to castration treatment, which is a reduction of available androgen/testosterone/DHT by chemical or surgical means. However, these cancers still show reliance upon hormones for androgen receptor activation.

The presence of prostate cancer or other steroid-dependent diseases can be confirmed using a variety of techniques known to those skilled in the art. The preferred method for confirming the presence of prostate cancer is to obtain a biopsy. In a prostate cancer biopsy, a tissue samples from the prostate is typically obtained via the rectum using a biopsy gun which inserts and removes special hollow-core needles. The tissue samples are then examined under a microscope to determine whether cancer cells are present, and to evaluate the microscopic features or Gleason score of any cancer found. Additional procedures for determining whether a human subject has prostate cancer include, but are not limited to, digital rectal examination, cystoscopy, transrectal ultrasonography, ultrasound, and magnetic resonance imaging.

Biological Samples

A number of the methods described herein include the step of obtaining a biological sample from the subject. A "biological sample," as used herein, is meant to include any biological sample from a subject that is suitable for analysis for detection of the HSD3B1(1245C) gene or the 3βHSD1 (367T) protein. Suitable biological samples include but are not limited to bodily fluids such as blood-related samples (e.g., whole blood, serum, plasma, and other blood-derived samples), urine, sputum, cerebral spinal fluid, bronchoalveolar lavage, and the like. Another example of a biological sample is a tissue sample. In some embodiments, the biological sample is a cancer cell or tissue including cancer cells. The HSD3B1(1245C) gene or the 3βHSD1(367T) protein can be assessed either quantitatively or qualitatively, and detection can be determined either in vitro or ex vivo.

The methods involve providing or obtaining a biological sample from the subject, which can be obtained by any known means including needle stick, needle biopsy, swab, and the like. In an exemplary method, the biological sample is a blood sample, which may be obtained for example by venipuncture.

A biological sample may be fresh or stored. Biological samples may be or have been stored or banked under suitable tissue storage conditions. The biological sample may be a tissue sample expressly obtained for the assays of this invention or a tissue sample obtained for another purpose which can be subsampled for the assays of this invention. Preferably, biological samples are either chilled or frozen shortly after collection if they are being stored to prevent deterioration of the sample.

The sample may be pretreated as necessary by dilution in an appropriate buffer solution, heparinized, concentrated if desired, or fractionated by any number of methods including but not limited to ultracentrifugation, fractionation by fast performance liquid chromatography (FPLC) or HPLC, or precipitation of apolipoprotein B containing proteins with dextran sulfate or other methods. Any of a number of standard aqueous buffer solutions at physiological pH, such as phosphate, Tris, or the like, can be used.

Subjects

The terms "individual," "subject," and "patient" are used interchangeably herein irrespective of whether the subject has or is currently undergoing any form of treatment. As used herein, the term "subject" generally refers to any vertebrate, including, but not limited to a mammal. Examples of mammals including primates, including simians and humans, equines (e.g., horses), canines (e.g., dogs), felines, various domesticated livestock (e.g., ungulates, such as swine, pigs, goats, sheep, and the like), as well as domesticated pets (e.g., cats, hamsters, mice, and guinea pigs). Treatment or diagnosis of humans is of particular interest.

Methods for Detecting the HSD3B1(1245C) Gene or 3βHSD1(367T) Protein

The gain of stability mutation leading to a gain of function in 3β-hydroxysteroid dehydrogenase type 1 (3βHSD1) can be identified in a subject by detecting either the variant form of either the gene (HSD3B1(1245C)) or the variant form of the protein (3βHSD1(367T)). The methods for determining the presence of the gain of function mutation differ depending on whether the gene or the protein is being detected. The gene or protein can be detected or measured by an analytic device such as a kit or a conventional laboratory apparatus, which can be either portable or stationary. In some embodiments, the levels of variant gene or protein may be compared to the level of corresponding internal standards in the sample or samples when carrying out the analysis to quantify the amount of the gene or protein being detected.

The HSD3B1(1245C) gene or the 3βHSD1(367T) protein are typically detected in a biological sample which has been obtained from the subject. However, in some embodiments, noninvasive imaging modalities for detecting this mutation are used. For example, administration of 18F-DHEA with PET imaging may be able to detect tumors that harbor the mutant enzyme because these tumors are anticipated to have great flux from DHEA to downstream androgen metabolites.

In some embodiments, the presence of the 3βHSD1 (367T) protein is determined. The presence and/or amount of the 3βHSD1(367T) protein in a biological sample can be determined using polyclonal or monoclonal antibodies that are immunoreactive with the 3βHSD1(367T) protein variant. Use of antibodies comprises contacting a sample taken from the individual with one or more of the antibodies; and assaying for the formation of a complex between the antibody and a protein or peptide in the sample. For ease of detection, the antibody can be attached to a substrate such as a column, plastic dish, matrix, or membrane, preferably nitrocellulose. The sample may be untreated, subjected to precipitation, fractionation, separation, or purification before combining with the antibody. Interactions between antibodies in the sample and the 3βHSD1(367T) protein are detected by radiometric, colorimetric, or fluorometric means, size-separation, or precipitation. Preferably, detection of the antibody-protein or peptide complex is by addition of a secondary antibody that is coupled to a detectable tag, such as for example, an enzyme, fluorophore, or chromophore. Formation of the complex is indicative of the presence of the 3βHSD1(367T) protein in the sample.

Antibodies immunospecific for 3βHSD1(367T) may be made and labeled using standard procedures and then employed in immunoassays to detect the presence of 3βHSD1(367T) in a sample. Suitable immunoassays include, by way of example, immunoprecipitation, particle immunoassay, immunonephelometry, radioimmunoassay (RIA), enzyme immunoassay (EIA) including enzyme-linked immunosorbent assay (ELISA), sandwich, direct, indirect, or competitive ELISA assays, enzyme-linked immunospot assays (ELISPOT), fluorescent immunoassay (FIA), chemiluminescent immunoassay, flow cytometry assays, immunohistochemistry, Western blot, and protein-chip assays using for example antibodies, antibody fragments, receptors, ligands, or other agents binding the target analyte. Polyclonal or monoclonal antibodies raised against 3βHSD1(367T) are produced according to established procedures. Generally, for the preparation of polyclonal antibodies, a protein or peptide fragment thereof is used as an initial step to immunize a host animal. A general review of immunoassays is available in Methods in Cell Biology v. 37: Antibodies in Cell Biology, Asai, ed. Academic Press, Inc. New York (1993), and Basic and Clinical Immunology 7th Ed., Stites & Ten, eds. (1991).

In some embodiments, the 3βHSD1(367T) protein is detected using a method other than an immunoassay. For example, the 3βHSD1(367T) protein can be detected using matrix-assisted laser desorption-ionization time-of-flight mass spectrometry (MALDI-TOF). The 3βHSD1(367T) protein can also be detected by purifying the 3βHSD1 protein and determining its sequence using peptide sequencing methods. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified and/or quantified using chromatographic and electrophoretic techniques to achieve partial or complete purification (or purification to homogeneity). Analytical methods particularly suited to the preparation of a pure peptide are immunohistochemistry, ion-exchange chromatography, exclusion chromatography; polyacrylamide gel electrophoresis; isoelectric focusing. A particularly efficient method of purifying peptides is fast protein liquid chromatography or even HPLC. Likewise, a variety of methods of protein sequencing are known to those skilled in the art. For example, the sequence may be identified using mass spectrometry or the Edman degradation reaction.

The 3βHSD1(367T) protein can also be detected based on its differing characteristics relative to the wild-type version of the protein. The inventors have demonstrated that the 3βHSD1(367T) protein is more resistant to ubiquitination and degradation than the 3βHSD1(367N) protein. Accordingly, the presence of the 3βHSD1(367T) protein can be detected using a ubiquitination and/or degradation assay. Likewise, the inventors have shown that the autocrine mobility factor receptor (AMFR), which is involved in protein degradation, shows a lower affinity for the 3βHSD1 (367T) protein than the 3βHSD1(367N) protein. Accordingly, the presence of the 3βHSD1(367T) protein can also be determined by evaluating the affinity of the 3βHSD1 for AMFR. Some tumors may also have somatic loss of expression of AMFR, or other methods of wild-type enzyme (3βHSD1(367N)) stabilization that might serve the tumor as a compensatory mechanism of protein stabilization, leading to increased DHT synthesis and treatment-resistance.

In some embodiments, the presence of the 3βHSD1 (367T) can be detected indirectly by observed the serum steroid profile. Assessment of the serum steroid profile could correlate with HSD3B1 genotype. For example, the mutant enzyme may be associated with an increase in the ratio of enzyme product vs. precursor (i.e., androstenedione/DHEA and progesterone/pregnenolone).

In some embodiments, the presence of the HSD3B1 (1245C) allele is determined. The presence and/or the level of the HSD3B1(1245C) allele can be determined by any now known or hereafter developed assay or method of detecting and/or determining expression level, for example, quantitative RT-PCR, Northern blot, real-time PCR, PCR, allele-specific PCR, pyrosequencing, SNP Chip technology, or restriction fragment length polymorphism (RFLP).

Many of the methods for determining a nucleotide sequence involve PCR. As used herein, the term "polymerase chain reaction" (PCR) refers to the methods of U.S. Pat. Nos. 4,683,195, 4,683,202, and 4,965,188, all of which are hereby incorporated by reference, directed to methods for increasing the concentration of a segment of a target sequence in a mixture of genomic DNA without cloning or purification. As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences. Accordingly, in some embodiments, the detecting the presence and/or level of the HSD3B1(1245C) allele comprises extending a primer that hybridizes to a sequence adjacent to the polymorphic nucleotide. In some embodiments, the determining the presence and/or level of the HSD3B1(1245C) allele comprises hybridizing a probe to a region that includes the polymorphic nucleotide.

In some embodiments, hybridization with complementary sequences may be used to detect the presence of the HSD3B1(1245C) allele based on the different characteristics of sequences that have a complete or incomplete sequence match. For example, as described herein, an asymmetric PCR assay can be used in which fluorescence melting reveals two distinct melting temperatures of the probe/target duplex that are specific for the amplified allele. This assay can be used to detect the HSD3B1(1245C) allele in the germline or in somatic cells.

Once the presence and/or levels of the variant form of either the gene (HSD3B1(1245C)) or the variant form of the protein (3βHSD1(367T)) have been determined, they can be displayed in a variety of ways. For example, the levels can be displayed graphically on a display as numeric values or proportional bars (i.e., a bar graph) or any other display method known to those skilled in the art. The graphic display can provide a visual representation of the amount of the variant gene or protein in the biological sample being evaluated.

Therapeutic Methods

The present invention provides methods of identifying a subject in need of treatment other than or in addition to steroid ablation. While steroid ablation is generally useful for treating steroid-dependent diseases, expression of the 3βHSD1(367T) protein results in resistance to steroid-depletion by catalyzing an otherwise rate limiting step in steroid formation by increasing the metabolic flux from dehydroepiandrosterone (DHEA) via the 5α-androstane-dione (5α-dione) pathway to DHT by protein resistance to ubiquitination and degradation. In some embodiments, steroid ablation is continued but an additional therapy is provided, while in other embodiments steroid ablation is discontinued and an additional, alternate therapy is provided.

A number of methods are known to those skilled in the art for carrying out steroid ablation. In some embodiments, steroid ablation can be carried out chemically. Examples of chemical treatments that can be used for steroid ablation include administration of surgical castration (orchiectomy), medical castration with use of GnRH-agonists (for example leuprolide or goserelin) or GnRH-antagonist (degarelix), androgen receptor antagonists, such as flutamide, bicalutamide, nilutamide, enzalutamide and cyproterone acetate, androgen synthesis inhibitors, such as abiraterone and ketoconazole, 5-alpha-reductase inhibitors (finasteride, dutasteride). The above treatments may be administered in combination with one another or in addition to a non-hormonal therapy. For example, medical or surgical castration may be combined with radiation therapy or radical prostatectomy. Castration may also be combined with chemotherapy, including but not limited to docetaxel chemotherapy.

Subjects with prostate cancer may have already been characterized as having castration-resistant prostate cancer. Subjects characterized as having castration-resistant prostate cancer can be treated using compounds such as docetaxel, cabazitaxel, radium-223, sipuleucel-T, abiraterone or enzalutamide as an alternative to steroid ablation.

Treatment other than steroid ablation can be provided to the subject if the HSD3B1(1245C) gene or 3βHSD1(367T) protein is expressed. For example, the subject can be treated using one or more of salvage cryotherapy, radiation therapy (e.g., external beam radiotherapy and brachytherapy), radical prostatectomy, proton therapy, or high intensity focused ultrasound as an alternative to steroid ablation. Radical prostatectomy is an operation to remove the prostate gland and some of the tissue around it, and may be done by open or laparoscopic surgery. Because these treatments destroy or remove the prostate cancer, they render moot the development of alternate metabolic pathways within the prostate cancer.

In other embodiments, treatment in addition to steroid ablation is provided to a subject in which the HSD3B1 (1245C) gene or 3βHSD1(367T) protein has been detected. For example, the subject can be treated with more intensive hormone therapy, such as the use of medical or surgical castration together with treatment with abiraterone or enzalutamide, prior to the development of castration-resistant prostate cancer.

Other embodiments of the invention make more direct use of the knowledge regarding the effect of the 3βHSD1(367T) protein on protein resistance to ubiquitination and degradation. For example, antibody specific for 3βHSD1(367T) could be used for specific immunotherapy against cells that harbor the somatic mutation. Genetic methods such as the use of siRNA or antisense RNA could also be used to suppress expression of 3βHSD1(367T). Another approach would be the use of a ubiquitination activator to overcome the resistance of the 3βHSD1(367T) or 3βHSD1(367N) in a tumor with otherwise stabilized 3βHSD1(367N) protein to ubiquitination. For example, tumors that have epigenetic silencing of the ubiquitin E3-ligase AMFR may be treated with a DNA methylation inhibitor or HDAC inhibitor to induce AMFR re-expression, leading to 3βHSD1 protein loss and tumor regression. Finally, assays in which compounds are tested for their ability inhibit the enzymatic activity of the 3βHSD1(367T) protein could be used to identify novel agents effective for the treatment of subjects with steroid-dependent disease in which the HSD3B1 (1245C) gene or 3βHSD1(367T) protein has been detected.

Candidate agents may be tested in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers, including prostate cancer (see, for instance, Polin et al., Investig. New Drugs, 15:99-108 (1997)). Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the cancer, including, for instance, cancer metastasis, cancer cell motility, cancer cell invasiveness, or combinations thereof.

Kits

The present disclosure also provides kits for guiding the treatment of steroid-dependent disease in a subject. The kits include one or more primers or probes capable of detecting 3βHSD1(367T) or HSD3B1(1245C), and a package for holding the primers or probes. A kit generally includes a package with one or more containers holding the reagents, as one or more separate compositions or, optionally, as an admixture where the compatibility of the reagents will allow. The kits may further include enzymes (e.g., polymerases), buffers, labeling agents, nucleotides, controls, and any other materials necessary for carrying out the detection of 3βHSD1(367T) or HSD3B1(1245C). Kits can also include a tool for obtaining a sample from a subject, such as a punch tool to obtain a punch-biopsy or needle biopsy.

In some embodiments, the kit includes a primer capable of detecting HSD3B1(1245C). For example, the kits may include suitably sized oligonucleotide primers that amplify a region of HSD3B1 including the A→C conversion. For example, in some embodiments, a region of from HSD3B1 including the A→C conversion and including from about 10 nucleotides to about 100 nucleotides can be used. Specific suitable primers are describing the Example, herein. The primers may be labeled.

In another aspect, kits for guiding treatment are provided that include an array and/or microarray, oligonucleotide primes that amplify from about nucleotide 1200 to about nucleotide 1300 portion of HSD3B1 and instructions for use. Alternately or in addition, primers may be provided that amplify from about nucleotide 1210 to about nucleotide 1280 of HSD3B1, from about nucleotide 1220 to about nucleotide 1270 of HSD3B1, from about nucleotide 1230 to about nucleotide 1260 of HSD3B1, from about nucleotide 1235 to about nucleotide 1250 of HSD3B1, or other portion that one of skill in the art would determine necessary or adequate to amplify and detect the presence of HSD3B1 (1245C) using PCR or other sequencing technology known to those skilled in the art.

In some embodiments, the kit includes a probe capable of detecting 3βHSD1(367T). A preferred type of probe is an antibody capable of specifically binding to 3βHSD1(367T). Examples of antibodies that can be used in the present disclosure include, but are not limited to, polyclonal antibodies, monoclonal antibodies, chimeric antibodies, human antibodies, humanized antibodies, recombinant antibodies, single-chain Fvs ("scFv"), an affinity matured antibody, single chain antibodies, single domain antibodies, F(ab) fragments, F(ab') fragments, disulfide-linked Fvs ("sdFv"), and antiidiotypic ("anti-Id") antibodies and functionally active epitope-binding fragments of any of the above.

As used herein, the term "specifically binding" refers to the interaction of the antibody with a second chemical species, wherein the interaction is dependent upon the presence of a particular structure (e.g., an antigenic determinant or epitope) on the chemical species; for example, an antibody recognizes and binds to a specific protein structure rather than to proteins generally.

The kits may also include a solid phase, to which the antibodies functioning as capture antibodies and/or detection antibodies in a sandwich immunoassay format are bound. The solid phase may be a material such as a magnetic particle, a bead, a test tube, a microtiter plate, a cuvette, a membrane, a scaffolding molecule, a quartz crystal, a film, a filter paper, a disc or a chip. The kit may also include a detectable label that can be or is conjugated to an antibody, such as an antibody functioning as a detection antibody. The detectable label can for example be a direct label, which may be an enzyme, oligonucleotide, nanoparticle chemiluminophore, fluorophore, fluorescence quencher, chemiluminescence quencher, or biotin. Test kits may optionally include any additional reagents needed for detecting the label.

The kit can also include instructions for using the kit to carry out a method of guiding treatment of steroid-dependent disease in a subject. In some embodiments, the steroid-dependent disease is a steroid-dependent cancer, such as prostate cancer. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

Examples have been included to more clearly describe a particular embodiment of the invention and its associated cost and operational advantages. However, there are a wide variety of other embodiments within the scope of the present invention, which should not be limited to the particular examples provided herein.

EXAMPLES

Example 1: A Genetic Mechanism Augments DHT Synthesis in Castration-Resistant Prostate Cancer The inventors show herein that CRPC sometimes expresses the 367T form of 3βHSD1 (3βHSD1(367T)), which increases metabolic flux from dehydroepiandrosterone (DHEA) via the 5α-androstanedione (5α-dione) pathway to DHT by protein resistance to ubiquitination and degradation rather than increased catalytic activity. Selection for 3βHSD1(367T) is evident from somatic mutation in human CRPC tumors, by loss-of-heterozygosity (LOH) of the wild-type copy in patients with germline heterozygous inheritance and from the generation and expression of the same somatic mutation occurring in a mouse xenograft model treated with abiraterone acetate.

Results

Cells with 3βHSD1(367T) have Increased Flux to DHT.

Figure 1:
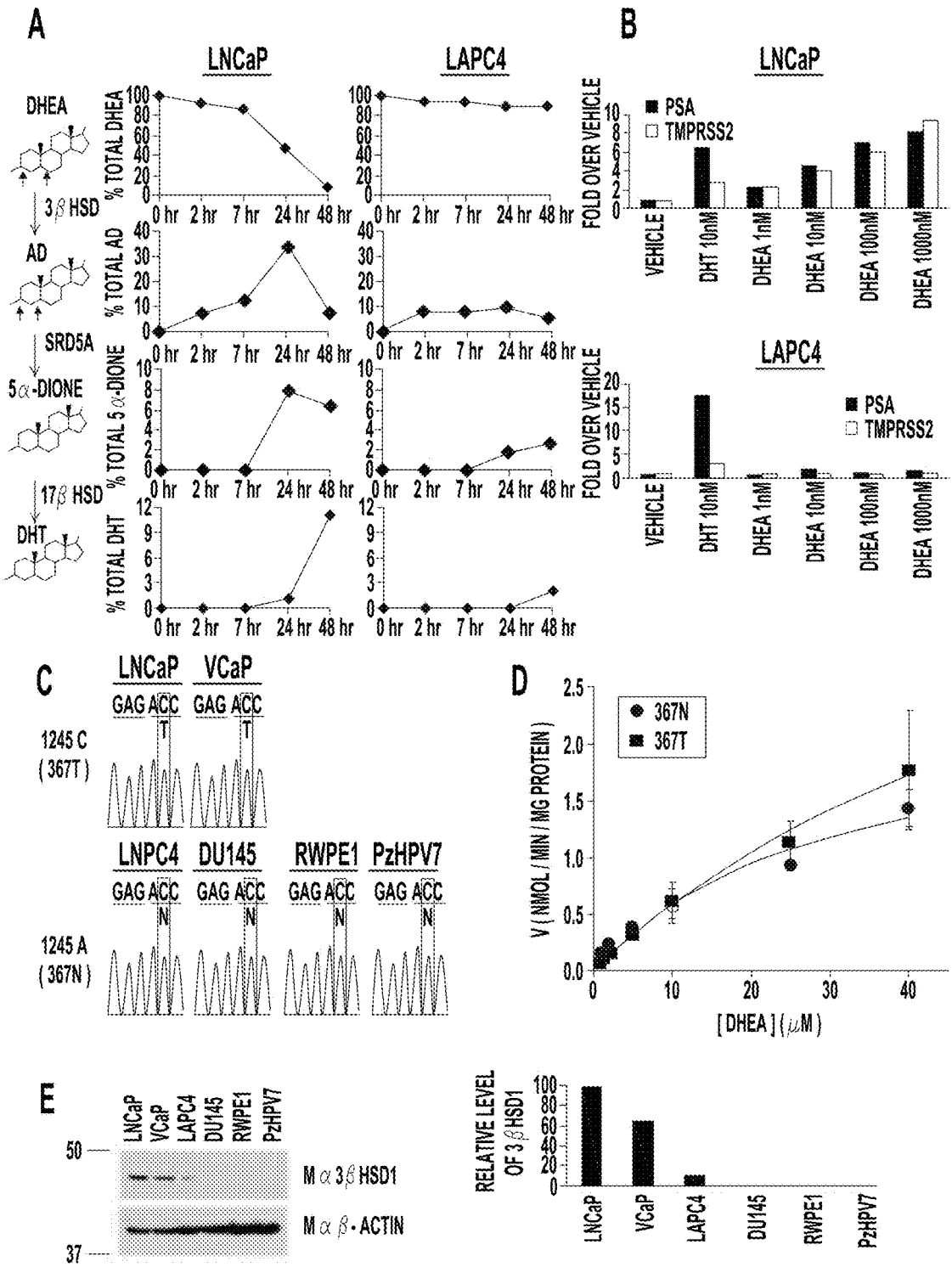
FIG. 1 provides graphs showing that the 3βHSD1(367T) protein encoded by mutant HSD3B1(1245C) increases flux from DHEA to AD, which is otherwise rate-limiting, en route to DHT and expression of AR-responsive genes. (A) Metabolic flux from [$^3$H]-DHEA (100 nM) to AD and downstream to 5α-dione and DHT is robust in LNCaP but limited in LAPC4. The metabolic pathway and steroid structures are shown, indicating sites of modification by 3βHSD1 in converting DHEA to AD. Steroids were quantitated at the indicated time points by HPLC. (B) DHEA induces PSA and TMPRSS2 expression in a concentration-dependent manner in LNCaP but not LAPC4. Expression was assessed by qPCR and normalized to RPLP0 and vehicle control. (C) A substitution converting A→C at position 1245 in HSD3B1 occurs in LNCaP and VCaP encoding a change from N→T at amino acid 367 in 3βHSD1. (D) Wild-type 3βHSD1(367N) and 3βHSD1(367T) have comparable kinetic properties. Michaelis-Menten plot of DHEA metabolism with 3βHSD1(367N) (circle) and 3βHSD1(367T) (square) enzyme. The $K_m$ for 3βHSD1(367N) and 3βHSD1(367T) protein are 32 and 77 μM, respectively. (E) Endogenous expression of 3βHSD1

Conversion of DHEA by 3βHSD1 to $\Delta^4$-androstenedione (AD) is a proximal step in peripheral tissues for metabolism from adrenal precursors to DHT. Lorence et al., Endocrinology 126, 2493-2498 (1990); Simard et al., Endocr Rev 26, 525-582 (2005). Two cell lines derived from patients with CRPC have widely disparate flux from DHEA to AD (FIG. 1A), despite comparable expression of transcripts encoding both 3βHSD1 and 3βHSD2 (FIG. 2A). Under the same conditions, LNCaP cells metabolize >90% of [$^3$H]-DHEA by 3βHSD enzymatic activity to AD after 48 hours, whereas LAPC4 cells metabolize only approximately 10% of [$^3$H]-DHEA. In LAPC4 but not LNCaP, apparent rate-limiting conversion of DHEA to AD en route to DHT via the dominant pathway (DHEA→AD→5α-dione→DHT) is further evident by limited accumulation of downstream metabolites and absence of DHEA concentration-dependent increases in AR-regulated PSA and TMPRSS2 (FIG. 1B). Sequencing the exons of both HSD3B isoenzymes reveals a single nonsynonymous substitution (FIG. 1C) at position 1245 of HSD3B1, converting A→C and exchanges an asparagine (N) for a threonine (T) at 3βHSD1 amino acid position 367 in LNCaP but not LAPC4. To further test the association between HSD3B1 sequence and steroid metabolism, other human prostate cell lines were investigated. Presence of wild-type (1245A) and variant (1245C) HSD3B1 sequence in other prostate cancer and immortalized prostate cell lines is also concordant with "slow" and "fast" flux from DHEA to AD, respectively (FIG. 2B). The kinetic properties of recombinant 3βHSD1(367N) and 3βHSD1(367T) proteins, however, do not explain the differences in steroid metabolism between cells expressing each protein (FIG. 1D). Western blot was performed to determine if the allele encoding 3βHSD1(367T) is associated with a greater amount of protein in these cells. Both models that encode for 3βHSD1(367T) have increased 3βHSD1 protein compared with the models that have wild-type sequence (FIG. 1E).

Androgen Deprivation Selects for HSD3B1(1245C).

The HSD3B1(1245C); 3βHSD1(367T) allele occurs as a germline SNP variant (rs1047303; 22% allele frequency) (Shimodaira et al., Eur J Endocrinol 163, 671-680 (2010)) but might also occur as a somatic mutation in prostate cancer. Although germline homozygous HSD3B1(1245C) inheritance cannot be ruled out, the most likely scenarios accounting for the sole presence of the HSD3B1(1245C) allele evident in both LNCaP and VCaP, given the low expected frequency of homozygous HSD3B1(1245C) inheritance, are either germline heterozygous inheritance followed by loss-of-heterozygosity (LOH) of the wild-type allele, or germline homozygous wild-type inheritance followed by somatic mutation of 1245 A→C. To identify the existence of these possible mechanisms of HSD3B1(1245C) selection in human tumors, matching germline and tumor DNA were sequenced from men with CRPC. Genomic DNA was isolated from CRPC and normal tissue from patients treated at the University of Texas Southwestern Medical Center (UTSW) and from the University of Washington (UW) rapid autopsy program. Of 40 men with CRPC, the germline of 25, 11 and 4 individuals are homozygous wild-type HSD3B1(1245A), heterozygous and homozygous variant HSD3B1(1245C), respectively. Three of 25 (12%) CRPC tumors with homozygous HSD3B1(1245A) inheritance have acquired the HSD3B1(1245C) allele (FIG. 3A). Expression of HSD3B1(1245C) transcript was confirmed in the one available fresh-frozen tumor. It is highly likely that the observation of 3 identical de novo mutations occurring in 25 patients is due to selection rather than chance alone, with a high degree of statistical significance (p=$1.47 \times 10^{-13}$), using the binomial method and assuming a mutation rate of 4 per 1,000,000 base pairs. Greenman et al., Nature 446, 153-158 (2007). Of 11 CRPC tumors with heterozygous inheritance, 3 (27%) have LOH of the HSD3B1(1245A) allele, resulting in the HSD3B1(1245C) allele being predominantly detectable (FIG. 3B). In these three tumors, LOH of adjacent heterozygous SNPs further confirms loss of this region of chromosome 1. In contrast, none of the 11 cases with heterozygous inheritance exhibited LOH of the HSD3B1(1245C) allele (FIG. 4A).

Two tumors (UW9 and UW25) with LOH of the HSD3B1 (1245A) allele had tissue remaining for additional studies. Consistent with the findings in LNCaP and VCaP that only have the HSD3B1(1245C) allele, both of these tumors have abundant detectable 3βHSD1 protein (FIG. 3C). In contrast, both tumors tested with heterozygous expression and homozygous HSD3B1(1245A) expression have little or no detectable 3βHSD1. mRNA quantitation by qPCR demonstrates that the increased 3βHSD1 protein abundance occurring specifically in the tumors with LOH is not attributable to transcript overexpression (FIG. 4B). Both tumors with LOH robustly express AR and PSA, suggesting that flux to DHT sustained by 3βHSD1 protein functions to elicit AR signaling (FIG. 3C).

Abiraterone inhibits CYP17A1 and weakly inhibits 3βHSD, further decreasing intratumoral androgen concentrations and extending survival in CRPC; therefore, conversion to the HSD3B1(1245C) allele encoding 3βHSD1 (367T) might permit sustained androgen synthesis despite lower availability of precursors. To determine if abiraterone treatment selects for the HSD3B1(1245C) allele, genomic DNA from LAPC4 xenograft tumors grown in orchiectomized mice treated with abiraterone or vehicle (n=8 mice per treatment) was isolated and sequenced. Li et al., Clinical Cancer Research 18, 3571-3579 (2012), The 1245C allele is detectable in 2 of 8 tumors (Abi #1 and Abi #2) in the abiraterone treatment group and no tumors in the vehicle group (FIG. 3D). To confirm expression of the somatically acquired mutation in the abiraterone group, cDNA clones were generated and sequenced. The mutant HSD3B1 (1245C) transcript encoding for 3βHSD1(367T) is confirmed in 12 of 21(57%) cDNA clones sequenced from Abi #1 and 7 of 26 (27%) clones from Abi #2. In contrast, the mutant transcript is not present in any of the 37 cDNA clones obtained from two vehicle treated LAPC4 xenograft tumors.

Blocking 3βHSD1(367T) Inhibits DHT Synthesis, the AR-Response and CRPC.

To determine the role of 3βHSD1(367T) expression in regulating flux from DHEA to DHT and AR stimulation, endogenous expression was silenced in LNCaP using 2 independent lentiviral shRNAs (FIG. 5A). Blocking 3βHSD1 expression with both shRNAs inhibits flux from DHEA to AD, resulting in little or no detectable conversion to downstream 5α-dione and DHT (FIG. 5B). Silencing mutant 3βHSD1 expression and blocking flux to DHT impedes the expression of AR-regulated PSA and TMPRSS2 (FIG. 5C), leading to inhibition of cell proliferation in vitro (FIG. 5D). In vivo, depletion of endogenously expressed mutant 3βHSD1 significantly hinders CRPC growth in surgically orchiectomized mice (FIG. 5E). CRPC tumors that eventually develop from cell lines initially expressing lentiviral shRNA knockdown constructs regain 3βHSD1 protein, probably from selection for cells that have lost the shRNA construct (FIG. 5F).

3βHSD1(367T) is Resistant to Ubiquitination and Degradation.

Endogenous expression of 3βHSD1(367T) appears to engender increased protein abundance compared to 3βHSD1(367N) expression (FIG. 1E). To determine if the underlying mechanism is due to an alteration in protein degradation, wild-type (HSD3B1(N)-HA) and (HSD3B1 (T)-HA) constructs were generated and transiently expressed, and protein levels were compared following inhibition of translation with cycloheximide (CHX) treatment. The 367 N→T mutation substantially increases protein half-life from 2.1 hours to 27 hours (FIG. 7A). Similar experiments with an alternative prostate cancer cell line (FIG. 6A) and with stable expression of lentiviral constructs confirm the longer half-life of 3βHSD1(367T) (FIG. 6B). To determine whether increased degradation of wild-type protein is reversible with proteasome inhibition, cells were treated with MG132. Pharmacologic proteasome inhibition increases endogenous wild-type 3βHSD1(367N) in LAPC4 but not 3βHSD1(367T) in LNCaP (FIG. 7B) and polyubiquitinated endogenous 3βHSD1(367N) accumulates with MG132 treatment in LAPC4 (FIG. 7C). In contrast, polyubiquitinated endogenous 3βHSD1(367T) is not increased in LNCaP with MG132 treatment (FIG. 6C). A direct comparison of ubiquitination between HA-tagged wild-type and mutant protein by Ni-agarose pull down demonstrates that 3βHSD1(367T) is resistant to polyubiquitination (FIG. 7D), explaining decreased vulnerability to proteasome-mediated degradation and longer protein half-life.

AMFR Binds 3βHSD1(367N) and is Required for Ubiquitination.

Mass spectrometry was employed to determine the lysine residue(s) ubiquitinated on 3βHSD1(367N). Ubiquitination is detectable on both K70 (FIG. 8A) and K352 (FIG. 8B) of 3βHSD1(367N). The effects of K352R and K70R single mutations and a double mutation on ubiquitination were assessed by Ni-agarose pull down (FIG. 8C). K352 appears to be a more critical site of ubiquitination than K70, and mutation of both sites decreases ubiquitination greater than either mutation alone. AMFR (autocrine mobility factor receptor, also known as gp78) is a membrane-anchored ubiquitin ligase that functions through the endoplasmic reticulum associated protein degradation (ERAD) pathway. Song et al., Mol Cell 19, 829-840 (2005). Eeyarestatin I (EerI) is a small molecule that inhibits protein degradation through the ERAD pathway. Wang et al., J Biol Chem 283, 7445-7454 (2008). Endogenous 3βHSD1(367N) protein increases in LAPC4 cells with EerI treatment, suggesting that the ERAD pathway is required for 3βHSD1(367N) degradation (FIG. 8D). Stable isotope labeling by amino acids in cell culture (SILAC) coupled with high-resolution mass spectrometry was employed to identify candidate ubiquitin ligases in an unbiased manner that preferentially associate with 3βHSD1(367N). Ong et al., Mol Cell Proteomics 1, 376-386 (2002). In this experiment, cells expressing 3βHSD1(367T)-HA and 3βHSD1(367N)-HA were grown in light and heavy media, respectively. AMFR was detected with a normalized protein ratio of 1.67 (derived from peptide ratios varying ≤17%) in a mixture of 3βHSD1 (367N)-HA and 3βHSD1(367T)-HA immunoprecipitations mixed in a 1:1 ratio, indicating preferential physical association with 3βHSD1(367N) protein. Immunoprecipitation of 3βHSD1(367N)-HA and 3βHSD1(367T)-HA, followed by AMFR immunoblot confirms a preferential physical association of AMFR with 3βHSD1(367N) protein (FIG. 8E). To assess the functional consequence of this interaction, AMFR was silenced using siRNA (FIG. 8F). AMFR knockdown increases the abundance of 3βHSD1 protein, demonstrating the requirement of AMFR for 3βHSD1 degradation through the ERAD pathway. In contrast, silencing the alternative ubiquitin ligase SKP2 by siRNA has no detectable effect on 3βHSD1.

3βHSD1(367T) Increases DHT Synthesis.

To determine if resistance to protein ubiquitination and degradation ascribed to 3βHSD1(367T) confers increased synthesis of DHT from precursor steroids, we expressed constructs that encode for 3βHSD1(367N), 3βHSD1(367T), or vector alone in LAPC4 cells, and assessed metabolic flux from [$^3$H]-DHEA to downstream steroids. LAPC4 cells transiently transfected with the construct encoding for 3βHSD1(367T) exhibit increased flux from DHEA→AD→5α-dione→DHT (FIG. 9A). Equivalent expression of both transcripts was confirmed by qPCR (FIG. 9B). Stable lentiviral expression of 3βHSD1(367T) similarly confers increased flux from DHEA→AD→5α-dione→DHT (FIG. 9C) with transcript expression comparable to wild-type (FIG. 9D). Finally, we determined that the 3βHSD1(367T) phenotype that accelerates flux from DHEA to DHT amplifies the response of androgen-regulated gene expression (FIG. 9E) and hastens the time to the development of CRPC xenograft tumors (FIG. 9F) in orchiectomized mice supplemented with DHEA to mimic human adrenal physiology. 3βHSD1(367T) tumors express higher levels of PSA transcript compared to 3βHSD1(367N) tumors, suggesting the presence of higher sustained DHT concentrations generated in 3βHSD1(367T) tumors (FIG. 9G). Together, these findings support a mechanism favoring genetic selection for the allele encoding 3βHSD1(367T) in the setting of androgen depletion.

Finally, FIG. 10 shows the effect of the presence of the HSD3B1 mutation on time to progression (TTP) in patients treated with standard androgen deprivation therapy (ADT). A high-resolution melting assay (validated with Sanger sequencing) to perform targeted germline genotyping in a cohort of 119 men receiving ADT for rising PSA in the post-prostatectomy setting at Cleveland Clinic. Germline DNA was obtained from benign archived prostatectomy tissues. Preliminary results using this assay reveal a strong correlation between the HSD3B1 variant and time to progression on ADT. Homozygous-variant men have a markedly shorter time to progression compared to men who are homozygous wild-type (31.8 months vs. 78.9 months), whereas heterozygotes have an intermediate clinical course (time to progression=49.7 months). In both cases the log-rank p value<0.05 when compared to the reference group (homozygous wild-type), and there is evidence of a gene-dosage effect (log-rank test for trend, p=0.011).

Discussion

A major mechanism of resistance to frontline gonadal T depletion (or castration) therapy is an acquired metabolic capability, which allows CRPC tumors to sustain sufficient DHT concentrations for AR stimulation and tumor progression. This study is the first to identify a gain-of-function mutation in the steroidogenic machinery that increases flux to DHT. Notably, whether utilizing the major adrenal pathway or possibly de novo steroidogenesis from cholesterol, 3β-hydroxl oxidation to 3-keto and $\Delta^{5\rightarrow4}$ isomerization by 3βHSD enzymatic activity is required for all pathways culminating in T and/or DHT synthesis. Adrenal DHEA and DHEA-sulfate are typically present in abundant concentrations in human serum. In the context of intratumoral 3βHSD1(367N) expression, the clinical response to gonadal T depletion probably occurs in part due to the limited contribution of adrenal precursors to intratumoral DHT. Augmented 3βHSD activity occurring through increased protein abundance with 3βHSD1(367T) would therefore serve to open the floodgates on a proximal and otherwise rate-limiting step for the synthesis of DHT, resulting in the development of CRPC. Notably, in the setting of heterozygous inheritance, 3βHSD1 protein expression is markedly higher in tumors that have lost the wild-type HSD3B1 (1245A) allele compared to tumors that retain the wild-type sequence (FIG. 2C). This finding might occur because expression and co-localization of the wild-type 3βHSD1 (367N) protein reinstates mutant 3βHSD1(367T) ubiquitination and subsequent degradation via dimerization or oligomerization. Nonetheless, engineered 3βHSD1(367T) expression engenders increased flux to DHT and development of CRPC despite endogenous 3βHSD1(367N) expression (FIG. 9). Therefore, the transition from sole 3βHSD1 (367N) expression to mixed expression to dominant 3βHSD1(367T) expression probably represents a stepwise selection for an increased capacity for DHT synthesis.

The population frequency of the HSD3B1(1245C) allele is approximately 22% but appears to vary widely by ethnicity (UCSC). Other studies suggest that the HSD3B1 (1245C) allele may raise aldosterone levels and increase the risk of essential hypertension. This is probably attributable to increased 3βHSD enzyme activity, which is required for aldosterone synthesis, although aldosterone is generally thought to require 3βHSD2. Interestingly, this phenotype appears to be more severe with homozygous HSD3B1 (1245C). The observation of extremely high aldosterone with homozygous HSD3B1(1245C) is consistent with higher enzymatic activity and stepwise selection for sole 3βHSD1(367T) expression that occurs in CRPC. HSD3B1 (1245C) has no consistent effect on risk of localized prostate cancer. Cunningham et al., Cancer Epidemiol Biomarkers Prev 16, 969-978 (2007).

Although abiraterone potently inhibits androgen synthesis, clinical studies of urinary androgen metabolites in patients with CRPC treated with this drug have demonstrated that the block is incomplete and that the synthesis of residual androgen precursors persists. Attard et al., J Clin. Endocrinol. Metab. 97, 507-516 (2012). This finding raises the possibility that tumor mechanisms that augment androgen synthesis from limited precursor steroids by increasing flux to DHT might contribute to abiraterone resistance. Chang, K. H., and Sharifi, N., Nat Rev Urol. 9(12):721-4 (2012). The inventor's data demonstrating the selection and expression of 3βHSD1(367T) in a xenograft model of abiraterone resistance suggest a genetic mechanism for clinical resistance to abiraterone and that pharmacologic inhibition of 3βHSD1 might be a viable therapeutic strategy to overcome this resistance against tumors expressing the mutant enzyme. Despite the potent activity of the AR antagonist enzalutamide, its affinity for the ligand-binding domain of AR is lower than the affinity of DHT. Tran et al., Science 324, 787-790 (2009). Increased metabolic flux from steroid precursors to DHT by 3βHSD1(367T) may therefore conceivably tip the scales in the favor of DHT and lead to enzalutamide resistance as well. The contribution of 3βHSD1(367T) in clinical resistance to abiraterone and enzalutamide, however, remain to be determined. While the inventor's demonstration is in a gain-of-function in a metabolic enzyme, rather than a signaling enzyme, the findings expose the opportunity for matching a mutant disease-driving enzyme biomarker with its cognate pharmacologic inhibitor.

Experimental Procedures

Steroid metabolism experiments were performed 12 hours after seeding cells by treatment with 1 mL serum-free medium containing [$^3$H]-labeled DHEA (100 nM, 300,000-600,000 cpm; PerkinElmer). Aliquots of medium were collected for up to 48 hours, treated with β-glucuronidase (1000 units; Sigma-Aldrich) at 65° C. for 4 hours. Deconjugated steroids were extracted, evaporated under nitrogen stream, dissolved in 50% methanol, injected on a Breeze 1525 system equipped with model 717 plus autoinjector (Waters Corp.) and steroid metabolites were separated on a Luna 150×3 mm, 3.0 μM $C_{18}$ reverse-phase column (Phenomenex). The column effluent was mixed with Liquiscint scintillation cocktail (National Diagnostics) and analyzed by a β-RAM model 3 in-line radioactivity detector (IN/US Systems). Steroid metabolism experiments with transient enzyme expression were performed with pCMV5-HSD3B1 (367N and 367T) constructs 24 hours after transfection and 12 hours after treatment with 25 μM cycloheximide (CHX). Steroid metabolism experiments with stable enzyme expression were performed after lentiviral infection with pLVX-Tight-Puro vector. Human tissues were obtained using IRB approved protocols at UT Southwestern and the University of Washington rapid autopsy program. Lentiviral constructs were made from miR30-styled shRNA sequences and cloned into the pGIPZ vector and infected cells expressing the constructs were selected with 2 μg/mL puromycin. Gene expression was performed by qPCR using the iTaq SYBR Green Supermix with the ROX kit (Bio-Rad) in an ABI-7500 Real-Time PCR machine (Applied Biosystems). Protein half-life was determined after transient transfection with pCMX-HSD3B1-HA (367N and 367T) plasmids, followed in 24 hours with 25 μM CHX in serum-free medium containing 100 nM DHEA. Cells stably expressing HA-tagged HSD3B1 (367N and 367T) in pLVX-Tight-Puro were used to determine protein half-life 24 hours after induction of protein expression with 2 ng/mL doxycycline and treatment with CHX.

Cell Lines.

LNCaP and DU145 were purchased from ATCC (Manassas, Va.) and cultured in RPMI 1640 medium with 10% fetal bovine serum. VCaP was purchased from ATCC and maintained in DMEM containing 10% fetal bovine serum. LAPC4 was generously provided by Dr. Charles Sawyers (Memorial Sloan Kettering Cancer, New York, N.Y.) and was maintained in Iscove's modified Dulbecco's medium (IMDM) with 10% fetal bovine serum. RWPE-1 was obtained from ATCC and cultured in Keratinocyte Serum Free Medium (K-SFM) (Invitrogen, Carlsbad, Calif.). PzHPV7 was generously provided by Dr. JT Hsieh (UT Southwestern) and maintained in PrEGM (Lonza, Allendale, N.J.). All cells except for VCaP were incubated in a 5% $CO_2$ humidified incubator. VCaP cells were grown in a 10% $CO_2$ humidified incubator.

Steroid Metabolism.

Cells (300,000-400,000 cells per well) were plated in 12-well plates coated with poly-L-ornithine. Twelve hours after seeding, medium was replaced with 1 mL serum-free medium containing [$^3$H]-labeled DHEA (100 nM, 300,000-600,000 cpm) purchased from PerkinElmer (Waltham, Mass.). Cells were incubated at 37° C. and aliquots of medium (0.25-0.3 mL) were collected for up to 48 hours. To hydrolyze the β-D-glucuronic acid group from steroids, 1000 units of β-glucuronidase (H. pomatia; Sigma-Aldrich, St. Louis, Mo.) were added to each aliquot and incubated at 65° C. for 4 hours. The deconjugated steroids were extracted with 1 mL 1:1 ethyl acetate:isooctane, and the reagents were evaporated under nitrogen stream. The dried samples were dissolved in 50% methanol and injected on a Breeze 1525 system equipped with model 717 plus autoinjector (Waters Corp., Milford, Mass.). The steroid metabolites were separated on a Luna 150×3 mm, 3.0 μM $C_{18}$ reverse-phase column (Phenomenex, Torrance, Calif.) with methanol/water gradients at 25° C. The column effluent was mixed with Liquiscint scintillation cocktail (National Diagnostics, Atlanta, Ga.) and analyzed by a β-RAM model 3 in-line radioactivity detector (LabLogic, Brandon, Fla.). All metabolism studies were performed in triplicate and repeated in independent experiments.

For steroid metabolism analysis of LAPC4 with transient enzyme expression, pCMV5-HSD3B1 was kindly provided by J. Ian Mason, sequenced and confirmed as encoding for 3βHSD1(367T). Lorence et al., Endocrinology 126, 2493-2498 (1990). The plasmid encoding wild type 3βHSD1 (367N) was derived by using Quick Change Site directed Mutagenesis kit (Agilent Technologies, Santa Clara, Calif.) with primer set (Forward: 5'-GGACCGGCACAAGGA-GAACCTGAAGTCCAAGACTCAG-3' (SEQ ID NO: 1) and Reverse: 5'-CTGAGTCTTGGACTTCAGGTTCTCCT-TGTGCCGGTCC-3' (SEQ ID NO: 2)). Plasmid DNA (20 ng) was transfected into 300,000 cells per well using Lipofectamine together with PLUS reagent (Life Technology, Grand Island, N.Y.). Twenty-four hours after transfection, cells were treated with 25 μM CHX for 12 hours and then steroids were analyzed as described above.

For steroid metabolism studies with stable expression, HSD3B1, wild type (367N) or mutant (367T) was PCR amplified with primer set (Forward: 5'-TCCGCGGCCGCG-GAGTGATTCCTGCTA-3' (SEQ ID NO: 3) and Reverse: 5'-AAGACGCGTGAGCTCTAGTAGTCAAAA-3' (SEQ ID NO: 4)) and sub-cloned into the pLVX-Tight-Puro vector (Clontech, Mountain View, Calif.) by Not1 and Mlu1 restriction sites. Lentiviral particles were packaged in 293T cells by co-transfecting 10 μg of each pLVX-Tight-Puro vector, pMD2.G, and psPAX2 vector. After lentiviral infection and 2 μg/m puromycin selection for 2 weeks, 300,000 cells per well were used for analysis of metabolic flux.

Human Tissues.

Matching CRPC and normal tissues (UW1-UW26) were obtained from the University of Washington rapid autopsy program with IRB approval number 39053. At UT Southwestern, matching tumor and normal tissues (UTSW1-UTSW14) were obtained using IRB approved protocols STU-032011-187 and STU-062010-212. All sequencing studies were independently repeated.

DNA Isolation and HSD3B1 Sequence Analysis.

Genomic DNA was prepared from cell lines and clinical samples (metastatic CRPC tumor and matched peripheral blood or normal tissue) using DNeasy Blood and Tissue Kit (QIAGEN, Germantown, Md.). PCR products of the promoter region, all exons, exon-intron junctions and the 3'-UTR were sequenced to identify mutations in HSD3B1. The primers and annealing temperature were described previously. Chang et al., Cancer Res. 62, 1784-1789 (2002). To sequence the 3' flanking region of HSD3B1, primer set (Forward: 5'-ATGTGGAGGGAGGTGTGAGT-3' (SEQ ID NO: 5) and Reverse: 5'-ACGGAGATGGGTCTCTTCCA-3'

(SEQ ID NO: 6)) were used with an annealing temperature of 62° C. Genotyping PCR reaction (50 µl) consisted of 30-100 ng genomic DNA, 1×PCR buffer with 0.2 mM dNTP, 0.2 µM of each primer, and 0.5 µl Phusion High-Fidelity DNA Polymerase (New England BioLabs Inc, Ipswich, Mass.). DNA sequencing and polymorphism analysis was carried out at the McDermott Center, UT Southwestern.

For HSD3B1 transcript analysis, total RNA was harvested and mRNA was reverse transcribed to cDNA by iScript cDNA synthesis kit (Bio-Rad). Cloning primer set (Forward: 5'-ACTGAATTCCAGGCCAATTTACACCTATCG-3' (SEQ ID NO: 7); Reverse: 5'-ACTCTCGAGTCAAACTAT-GTGAAGGAATGGA-3' (SEQ ID NO: 8)) were used to PCR amplify the 3' region of HSD3B1 exon 4 and subcloned into the pCMX vector. Colonies with inserts were picked for sequencing.

Gene Knockdown by Lentiviral Vector or RNA Interference.

Lentiviral vector construction, viral packaging and infection were performed as previously described. Chang et al., Proc. Natl. Acad. Sci. USA, 108, 13728-13733 (2011). Briefly, three miR30-styled shRNA sequences (#1: 5'-TGCTGTTGACAGTGAGCGACCTCATACA-GAAAGTGACAAGTAGTGAAGCCACAGAT GTACTT-GTCACTTTCTGTATGAGGCTGCCTACTGCCTCGGA-3' (SEQ ID NO: 9); #2: 5'-TGCTGTTGACAGTGAGCGAAGAGGAAAGAC-CATGTGGTTTTAGTGAAGCCACAGAT GTAAAAC-CACATGGTCTTTCCTCTGTGCCTACTGCCTCGGA-3' (SEQ ID NO: 10)) against HSD3B1 were PCR amplified and cloned into the pGIPZ vector (Open Biosystems, Huntsville, Ala.) and confirmed by sequencing. Virus packaging was carried out in 293T cells by co-transfecting 10 µg each of pGIPZ, pMD2.G, and psPAX2 vector. To increase transduction efficiency, 30 mL supernatant containing lentiviral particles were collected, filtered with a 0.45 µm nitrocellulose membrane and concentrated by ultracentrifugation at 19,000 rpm for 2 hours and 20 minutes at room temperature without brake. Pellets containing viral particles were re-suspended with 3 mL RPMI 1640 with 10% FBS and 1 mL was used to infect LNCaP cells supplemented with polybrene (6 µg/mL). After 24 hours, the infected cells were selected with 2 µg/mL puromycin for 2 weeks before evaluation for knockdown efficiency.

For RNA interference, 25 nM siGENOME Human siRNA (Thermo Fisher Scientific, Waltham, Mass.) was transfected into LAPC4 ($1\times10^6$ cells per well in 6 well plate coated with poly-L-ornithine) by Lipofectamine RNAiMax (Life Technology, Grand Island, N.Y.). Cell lysate was collected at 48 hours after transfection and knockdown efficiency was determined by Western blot with rabbit anti-AMFR and rabbit anti-SKP2.

Mouse Xenograft Studies.

Mouse xenograft studies and abiraterone acetate treatment were done as described in detail previously. Li et al., Clin Cancer Res 18, 3571-3579 (2012). Briefly, male NOD/SCID mice 6 to 8 weeks of age were obtained from the UT Southwestern Animal Resources Center, underwent surgical orchiectomy and a DHEA pellet (5 mg 90-day sustained-release) implantation and 2 days later underwent subcutaneous injection with $7\times10^6$ LAPC4 cells. Tumors reaching 300 mm$^3$ volume were treated with intraperitoneal abiraterone acetate or vehicle (n=8 mice per treatment) once daily for 5 days per week for 4 weeks. Tumors were fresh frozen upon mouse sacrifice. For the studies of mutant 3βHSD1 knockdown, LNCaP cells ($7\times10^6$) stably expressing shHSD3B1 #1, #2 and shCTRL were subcutaneously injected with matrigel into eugonadal NOD/SCID mice (n=15 per group). Mice with tumors reaching 100 mm$^3$ volume underwent surgical castration and DHEA pellet implantation. Time from castration to tumor volume ≥600 mm$^3$ was assessed. For the comparison between wild type and mutant 3βHSD1, LAPC4 cells ($7\times10^6$) stably expressing pLVX-Tight-Puro-HSD3B1 (367N) or pLVX-Tight-Puro-HSD3B1 (367T) were subcutaneously injected into surgically orchiectomized NOD/SCID mice supplemented with a DHEA (5 mg 90-day sustained-release) pellet. Tumor diameters were measured by digital calipers two or three times per week.

Cell Proliferation Studies.

LNCaP was seeded in triplicate at 100,000 cells/well in 12-well plates coated with poly-L-ornithine and grown in the presence of 20 nM DHEA or vehicle control for up to 7 days. Relative cell numbers were determined by staining nucleic acid with Hoechst. Kan et al., Cancer Res 67, 9862-9868 (2007). Briefly, cells were washed with PBS and frozen with 250 µL Milli-Q water. To stain the nucleic acid, plates were thawed completely and 500 µL Hoechst staining buffer (Hoechst 10 µg/mL in 1 mM EDTA, 2M NaCl and 10 mM Tris, pH=7.5) was added to each well. After shaking plates gently in a dark at room temperature for 2 hours, fluorescence in each well was determined by excitation at 360 nm and measuring emission at 460 nm with a plate reader. DNA quantities were estimated by comparison to the standard curve.

Gene Expression.

To accurately quantitate each gene transcript, qPCR was performed as previously described. Chang et al., 2011. Briefly, the iTaq SYBR Green Supermix with ROX kit (Bio-Rad, Hercules, Calif.) was applied for the thermocycling reaction in an ABI-7500 Real-Time PCR machine (Applied Biosystems, Foster City, Calif.). Total RNA (1 µg) collected by RNeasy kit (QIAGEN) was used in a RT reaction with the iScript cDNA synthesis kit (Bio-Rad). The qPCR analysis was carried out in triplicate with the following primer sets: HSD3B1 (Forward: 5'-CCATGTGGTTT-GCTGTTACCAA-3' (SEQ ID NO: 11); Reverse: 5'-TCAAAACGACCCTCAAGTTAAAAGA-3' (SEQ ID NO: 12)), PSA (Forward: 5'-GCATGGGATGGGGAT-GAAGTAAG-3' (SEQ ID NO: 13); Reverse: 5'-CAT-CAAATCTGAGGGTTGTCTGGA-3' (SEQ ID NO: 14)), TMPRSS2 (Forward: 5'-CCATTTGCAGGATCTGTCTG-3' (SEQ ID NO: 15); Reverse: 5'-GGATGTGTCTTGGGGAG-CAA-3' (SEQ ID NO: 16)), the housekeeping gene large ribosomal protein P0 (RPLP0) (Forward: 5'-CGAGGGCACCTGGAAAAC-3' (SEQ ID NO: 17); Reverse: 5'-CACATTCCCCCGGATATGA-3' (SEQ ID NO: 18)) and GAPDH (Forward: 5'-AGAAGGCTGGGGCT-CATTTG-3' (SEQ ID NO: 19); Reverse: 5'-AGGGGC-CATCCACAGTCTTC-3' (SEQ ID NO: 20)). Each mRNA transcript was quantitated by normalizing the sample values to RPLP0 or GAPDH and to non-silencing control cells (for knockdown) or to vehicle treated cells (for steroid treated cells). All gene expression studies were repeated in independent experiments.

Enzyme Kinetics.

Recombinant human 3βHSD1 was expressed in *S cerevisciae* strain W303B using yeast vector V10-3βHSD1 for wild-type and 367T proteins, and microsomes were prepared as described. Li et al., 2012. Incubations containing [$^3$H]-DHEA (0.5-40 µM, 100,000 cpm) and 25 µg microsomal protein in 0.25 ml of 50 mM potassium phosphate (pH 7.4) were pre-incubated at 37° C. for 1 min before initiating the reaction with NAD$^+$ (0.1 mM). After 20 min at 37° C., the steroids were extracted with 1 ml dichloromethane, concentrated, and resolved on an Agilent 1260 HPLC equipped with a Kinetex 2.1×100 mm, 2.6 μm $C_{18}$ reverse-phase column (Phenomenex, Torrance, Calif.) using methanol-water gradients at 0.4 ml/min. The column effluent was analyzed with a β-RAM4 (LabLogic) in-line scintillation counter and Bio-SafeII cocktail (Research Products International). Means of triplicate determinations were plotted as v versus [S], and kinetic constants $K_m$ and $V_{max}$ were obtained by fitting the data to the Michaelis-Menten equation using Origin version 7.5.

Protein Half-Life Determination.

For transient expression, LAPC4 or DU145 cells ($1 \times 10^6$ cells per well) were seeded on poly-L-ornithine coated 6-well plate for 24 hours. Constructs encoding wild type 3βHSD1(367N) or 3βHSD1(367T) protein (pCMX-HSD3B1-HA plasmids; 150 ng per well) were transfected using Lipofectamine, together with PLUS reagent (Life Technology). After 24 hours, cells were treated with 25 μM CHX (Sigma-Aldrich, St. Louis, Mo.) in serum-free IMDM containing 100 nM DHEA for up to 8 hours. Cell lysates were harvested using RIPA buffer with Protease Inhibitor Cocktail (Roche).

For stable expression of 3βHSD in LAPC4, cells expressing wild type 3βHSD1(367N) or 3βHSD1(367T) HA-tag fused to HSD3B1 were constructed by pLVX-Tight-Puro vector system (Clontech, Mountain View, Calif.). One million cells were seeded on each well of poly-L-ornithine coated 6-well plates in IMDM containing 10% Tet System Approved FBS (Clontech). Expression of 3βHSD was induced by 2 ng/mL doxycycline for 24 hours. CHX treatment and lysate collection were performed as described above. Proteins were analyzed by SDS-PAGE and Western blot. Films were scanned and quantitated by ImageJ. Protein half-life calculation was done as previously described. Bloom et al., Cell 115, 71-82 (2003). Briefly, 3βHSD1 signal was normalized to β-actin and time zero. The $t_{1/2}$ was calculated by an equation derived from the logarithmic trend line. All experiments were independently repeated.

Western Blot Analysis and Immunoprecipitation.

For Western blot analysis, whole cell protein extract was harvested using RIPA buffer (Sigma-Aldrich) with protease inhibitor cocktail (Roche). Protein concentration was determined by BCA Protein Assay Reagent (Thermo Scientific, Rockford, Ill.), and 20 μg protein was resolved by 8.5% SDS-PAGE. The protein was transferred to a PVDF membrane and was detected by mouse anti-3βHSD1 (Sigma), rabbit anti-HA (Santa Cruz Biotechnology, Santa Cruz, Calif.), and mouse anti-β-actin (Sigma) antibodies. To determine the role of the ERAD pathway in 3βHSD1 stability, cells were treated with Eeyarestatin (Sigma) for 6 hours before harvesting cell lysate.

To purify endogenous ubiquitin modified 3βHSD1, total cell lysate from ten million LAPC4 cells treated with 10 μM MG132 for 6 hours (EMD Millipore, Billerica, Mass.) was collected with IP lysis buffer (20 mM HEPES pH 7.9, 1 mM EDTA, 1 mM EGTA, 150 mM NaCl, 10 mM glycerol phosphate, 10 mM sodium pyrophosphate, 1 mM dithiothreitol, 1 mM NaF, 1 mM $Na_3VO_4$, 0.1% Nonidet P-40), supplemented with protease inhibitor cocktail and 20 mM N-ethylmaleimide (Sigma). Pre-cleared lysate was incubated with mouse anti-ubiquitin antibody (Santa Cruz) at 4° C. for 3 hours and followed by adding 40 μl of Protein AG UltraLink Resin (Thermo Scientific) for another hour for pull down. After extensive washing with lysis buffer, the purified proteins were eluted with 25 μl 2×SDS sample buffer and analyzed by Western blot.

For co-immunoprecipitation of 3βHSD1 and AMFR, 4 dishes of 293T cells (at 60% confluence) were transfected with 5 μg of wild type 3βHSD1(367N) or 3βHSD1(367T) pCMX-HSD3B1-HA by polyethylenimine (Polysciences, Warrington, Pa.) for 36 hours. Immunoprecipitation assay was performed as described above. All immunoprecipitation studies were repeated with independent experiments.

In Vivo Ubiquitination Assay.

For purification of 6×His-ubiquitin ("6×His" disclosed as SEQ ID NO: 21) conjugated proteins, experiments were conducted as previously described, with minor modifications. Rodriguez et al., EMBO J 18, 6455-6461 (1999); Xirodimas et al., Cell 118, 83-97 (2004). Briefly, HEK293T cells were transfected with pcDNA3-6×His-ubiquitin ("6× His" disclosed as SEQ ID NO: 21) together with wild-type 3βHSD1(367N) or 3βHSD1(367T) pCMX-HSD3B1-HA for 36 hours. Transfected cells were harvested by scraping in ice-cold PBS. Twenty percent of the cell suspension was pelleted and lysed with RIPA lysis buffer. Heterologously-expressed proteins were analyzed by Western blot. The remaining cells were pelleted and lysed with 4 mL lysis buffer (6 M guanidine-HCl, 0.1 M $Na_2HPO_4/NaH_2PO_4$, 0.01 M Tris/HCl, pH 8.0, 5 mM imidazole, and 10 mM β-mercaptoethanol). Proteins covalently conjugated by 6×His-ubiquitin ("6×His" disclosed as SEQ ID NO: 21) were pulled down by adding 40 μl Ni-NTA-agarose (QIAGEN Inc, Valencia, Calif.), incubated at room temperature for 2 hours and successively washed with the following buffers: (1) 6 M guanidine-HCl, 0.1 M $Na_2HPO_4/NaH_2PO_4$, 0.01 M Tris/HCl, pH 8.0, 5 mM imidazole plus 10 mM β-mercaptoethanol; (2) 8 M Urea, 0.1 M $Na_2HPO_4/NaH_2PO_4$, 0.01 M Tris/HCl, pH 8.0, 10 mM imidazole, 10 mM β-mercaptoethanol plus 0.1% Triton X-100; (3) 8 M urea, 0.1 M $Na_2HPO_4/NaH_2PO_4$, 0.01 M Tris/HCl, pH 6.3, 10 mM β-mercaptoethanol (buffer A), 20 mM imidazole plus 0.2% Triton X-100, twice; (4) buffer A with 10 mM imidazole plus 0.1% Triton X-100; (5) buffer A with 10 mM imidazole plus 0.05% Triton X-100. After the last wash, the proteins were eluted with 25 μl 2×SDS sample buffer containing 200 mM imidazole and 10 μL of elute was then analyzed by SDS-PAGE and Western blot. To determine the ubiquitin conjugation sites, lysine residues were replaced with arginine by using Quick Change Site directed Mutagenesis kit (Agilent Technologies) with primer set (K70R Forward: 5'-GAT GAG CCA TTC CTG AGG AGA GCC TGC CAG GAC-3' (SEQ ID NO: 22); K70R Reverse: 5'-GTC CTG GCA GGC TCT CCT CAG GAA TGG CTC ATC-3' (SEQ ID NO: 23); K352R Forward: 5'-GAG GAA GCC AAG CAG AGA ACG GTG GAG TGG GTT-3' (SEQ ID NO: 24); K352R Reverse: 5'-AAC CCA CTC CAC CGT TCT CTG CTT GGC TTC CTC-3' (SEQ ID NO: 25)). Ubiquitination studies were repeated with independent experiments.

Mass Spectrometry

Materials.

1M triethylammonium bicarbonate (TEAB) solution, dl-dithiothreitol (DTT), iodoacetamide, and proteomics sequencing grade trypsin were purchased from Sigma. LC/MS grade acetonitrile and LC/MS grade trifluoroacetic acid (TFA) were purchased from Fisher Scientific.

In-Gel Digestion.

Protein samples were separated by SDS-PAGE and stained with SimplyBlue SafeStain (Invitrogen) following the standard procedure. Briefly, the gel was rinsed with ultrapure water 3 times for 5 minutes and stained with 20 mL SimplyBlue SafeStain for 1 hour at room temperature. After washing twice with 100 mL ultrapure water for 1 hour, each gel lane was then cut into three pieces such that each would contain roughly equal amounts of proteins. Each excised gel band was then further chopped down into 1 mm cubes. In-gel digestion was performed following the protocol below. Coomassie blue stain was removed by a 30 min incubation at 37° C. in 50 mM triethylammonium bicarbonate (TEAB)/acetonitrile (1:1, v/v). Gel pieces were dehydrated with acetonitrile at room temperature, followed by reduction/alkylation using DTT and iodoacetamide. Gel pieces were then dehydrated with acetonitrile and rehydrated with trypsin solution (400 ng/µg in 50 mM acetic acid). Trypsin digestion was carried out at 37° C. overnight. Peptides were extracted after 30 min incubation at 37° C. with extraction buffer to a final concentration of 50% acetonitrile and 3.3% TFA. All steps were carried out on a thermomixer shaker (Eppendorf, N.J.) unless stated otherwise. Extracts were dried in vacuum centrifuge. Salts were removed using Oasis HLB µElution plate (Waters, MA) before LC-MS/MS analysis.

LC-MS/MS Analysis.

One-dimensional liquid chromatography was performed on an Ultimate 3000 nano HPLC system (Dionex), equipped with a 75 µm i.d.×50 cm Thermo Scientific Easy-Spray column packed with 2 µm resin. Separation of peptides was carried out at 350 nl/min by a 200 min linear gradient of 1% to 25% acetonitrile in 0.1% formic acid. Column temperature was raised and maintained at 60° C. using an Easy-Spray source (Thermo Electron). Mass spectrometric analyses were performed on a QExactive instrument (Thermo Electron) using a data-dependent top 20 method, with the full-MS scans acquired at 70K resolution (at m/z 200) and MS/MS scans acquired at 17.5K resolution (at m/z 200). Under-fill ratio was set at 0.1%, with a 3 m/z isolation window and fixed first mass of 100 m/z for the MS/MS acquisitions. The charge exclusion was applied to exclude the unassigned and singly charged species, and dynamic exclusion was used with a duration of 15 sec. SILAC MS data were analyzed using MaxQuant (version 1.3.0.5) with default parameters, except that GlyGly(K) was specified as a variable modification. Cox, J., and Mann, M., Nat Biotechnol 26, 1367-1372 (2008).

Example 2: Germline/Somatic Mutation Detection Assay

Somatic Mutation Detection (PCR1):

The (N367T) somatic mutation in the wild type individuals is detected through an asymmetric PCR assay using an unlabelled 3'-locked Nucleic acid (LNA) specific to the wild type allele that blocks the amplification of the wild type allele allowing the mutant allele to be preferentially amplified. The endpoint fluorescence melting of the DNA saturating dye results in a melting kinetic that is specific to the probe/mutant target duplex which can be compared to the melting temperature of the probe/wild type target duplex resulting from a second non-blocking PCR that amplifies both alleles equally. The assay is sensitive to 0.75% of the mutant allele in the total allele population.

For each sample, prepare two PCR mixtures as shown in Table 1 below:

TABLE 1

|  | 1 reaction | Multiple reactions |
| --- | --- | --- |
| Component | 20 µl reaction | 80 |
| Lightcycler HRM LCGreen Master mix | 8 | 640 |

TABLE 1-continued

|  | 1 reaction | Multiple reactions |
| --- | --- | --- |
| Forward Primer (1 µM) | 1 | 80 |
| Reverse Primer (10 µM) | 1 | 80 |
| LNA Probe6 (10 µM) | 1 | 80 |
| DNA (10 ng/mM) | 4 |  |
| H₂0 | 5 | 400 |
| Total | 20 |  |

For PCR1, the following "pre-PCR" cycles are run, as shown in Table 2:

TABLE 2

| Step | Temp | Time |
| --- | --- | --- |
| Initial denaturing | 95° C. | 2 minutes |
| 30 cycles | 94° C./66° C. | 30 seconds each temp. |

Both PCR1 (after the pre-PCR cycles) and PCR2 are run through the cycles shown in Table 3:

TABLE 3

| Step | Temp | Time |
| --- | --- | --- |
| Initial denaturing | 95° C. | 2 minutes |
| 60 cycles | 94° C. | 30 seconds |
|  | 66° C. | 30 seconds |
|  | 75° C. | 30 seconds |
| Melting Curve | 95° C. | 30 seconds |
|  | 25° C. | 60 seconds |
|  | 50° C. | 15 seconds |
|  | Ramp rate (0.3-1% to 95° C. | 15 seconds |

Germline SNP Detection (PCR2):

The (N367T) germline SNP detection assay was designed using a wild type specific unlabelled Locked Nucleic Acid (LNA) hybridization probe in an asymmetric PCR in the presence of a DNA saturating dye. 219 bp-amplicon is amplified using the LC-Green Lightscanner® Master Mix (Biofire Defense, Salt Lake City, Utah) at 1:10 primer ratio. After PCR is complete, an endpoint fluorescence melting reveals two distinct melting temperatures of the probe/target duplex that are specific for the amplified allele (73.6° C. for wild type and 71.5° C. for mutant). The heterozygous genotype shows two melting peaks. 3BHSD2 and the four 3BHSD1 pseudogenes will not interfere in this genotyping assay because of the high specificity of the primers and the stringency of the PCR. The assay showed 100% concordance when compared to sequencing as a reference method. The assay was validated for 40 ng of DNA extracted from fresh frozen and FFPE tissues.

Results of carrying out the assays are shown in FIG. 11. The purpose behind the germline mutation assay (PCR2), which is carried out using the same protocol used for PCR1, is to genotype and detect the somatic mutation at the same time PCR2. If only known wild type samples are being tested, it is unnecessary. The PCR2 assay also enables one to differentiate between heterozygous and somatic mutations (they will all be mutant in PCR1) and to detect loss of heterozygosity.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of treating castration-resistant prostate cancer in a subject in need thereof, comprising:
   determining that a cytosine nucleotide is present at position 1245 of the HSD3B1 gene or a threonine is present at position 367 of the 3βHSD1 protein by assaying a biological sample from the subject, and
   administering treatment to the subject selected from the group consisting of salvage cryotherapy, radiation therapy, radical prostatectomy, proton therapy, and high intensity focused ultrasound,
   or continuing steroid ablation together with administration of an androgen receptor antagonist, administration of an androgen synthesis inhibitor, or administration of a 3βHSD1 inhibitor to the subject.

2. The method of claim 1, wherein the biological sample is a blood sample.

3. The method of claim 1, wherein the treatment is one or more of salvage cryotherapy, radiation therapy, or radical prostatectomy.

4. The method of claim 1, wherein the subject is also treated using steroid ablation.

5. The method of claim 1, wherein the treatment is administration of abiraterone or enzalutamide.

6. The method of claim 1, wherein the method includes determining that a threonine is present at position 367 of the 3βHSD1 protein.

7. The method of claim 6, wherein the presence of threonine at position 367 of the 3βHSD1 protein is determined using an immunoassay.

8. The method of claim 1, wherein the method includes determining that a cytosine nucleotide is present at position 1245 of the HSD3B1 gene.

9. The method of claim 8, wherein the presence of a cytosine nucleotide at position 1245 of the HSD3B1 gene is determined using PCR methods, sequencing methods, RFLP, or SNP Chip technology.

10. The method of claim 1, wherein the subject is human.

11. The method of claim 1, further comprising the step of obtaining a biological sample from the subject.

* * * * *